United States Patent [19]

Sims

[11] Patent Number: 5,843,884
[45] Date of Patent: Dec. 1, 1998

[54] C9 COMPLEMENT INHIBITOR

[75] Inventor: Peter J. Sims, Mequon, Wis.

[73] Assignee: Oklahoma Medical Research Foundation, Oklahoma City, Okla.

[21] Appl. No.: 559,492

[22] Filed: Nov. 15, 1995

[51] Int. Cl.⁶ .............................. A01N 1/00; A61K 38/00; A61K 39/395; C07K 16/00
[52] U.S. Cl. ........................... 514/2; 530/324; 530/387.1; 530/387.2; 424/131.1; 424/138.1
[58] Field of Search .............................. 424/138.1, 131.1; 536/23.1; 530/300, 350, 324, 387.1, 387.2; 514/2

[56] References Cited

U.S. PATENT DOCUMENTS

| | | | |
|---|---|---|---|
| 3,625,214 | 12/1971 | Higuchi .................................... | 128/260 |
| 4,244,946 | 1/1981 | Rivier et al. ............................. | 424/177 |
| 4,305,872 | 12/1981 | Johnston et al. ...................... | 260/112.5 |
| 4,316,891 | 2/1982 | Guillemin et al. ....................... | 424/177 |
| 4,629,784 | 12/1986 | Stammer ................................. | 530/328 |
| 4,789,734 | 12/1988 | Pierschbacher ......................... | 530/395 |
| 4,792,525 | 12/1988 | Ruoslaghti et al. ..................... | 435/240 |
| 4,906,474 | 3/1990 | Langer et al. ............................ | 424/428 |
| 4,925,673 | 5/1990 | Steiner et al. ............................ | 424/455 |

FOREIGN PATENT DOCUMENTS

WO 93/01286  1/1993  WIPO .

OTHER PUBLICATIONS

Agrawal, et al., "Oligodeoxynuleoside Phosphoramidates And As Inhibitors of Human Immunodeficiency Virus, "*Proc. Natl. Acad. Sci. USA,* 85:7079–7083 (1988).
Askew, et al,*J. Am. Chem. Soc.,*111:1082–1090 (1989).
Chang, et al., "Identity of a Peptide Domain of Human C9 That Is Bound by the Cell–surface Complement Inhibitor, CD59",*J. Bio. Chem.,* 269 (42):26424–26430 (1994).
Clackson, et al., *Nature,* 352:624–688 (1991).
Daugherty, et al., *Nucl. Acids Res.,* 19:2471–2476 (1991).
Davies, et al., *J. Exp. Med.,*170:637–654 (1989).
Davies, et al., *Immunol. Res.,*12:258–275 (1993)
Dupuis, et al., *Mol. Immunol.,*30:95–100 (1993)
Gregoriadis, Chapter 14. "Liposomes", *Drug Carriers in Biology and Medicine,* 287–341 (Academic Press, 1979).
Hamilton, et al., "Regulatory Control of the Terminal Complement Proteins at the Surface of Human Endothelial Cells: Neutralization of a C5b–9 Inhibitor by Antibody to CD59" *Blood,*76:2572–2577 (1990).
Hamilton, et al., "Complement Proteins C5b–9 Induce Vesiculation of the Endothelial Plasma Membrane and Expose Catalytic Surface for Assembly of the Prothrombinase Enzyme Complex " *J. Bio. Chem.,* 265:3809–3814 (1990).
Harada, et al., *J. Oral Pathol. Med.*(Denmark), 22(f):145–152 (1993).
Hatanaka, et al.,*Biochim. Biophys. Acta Protein Struct. Mol. Enzymol.* 1209:117–122 (1994).
Hattori, et al., "Stimulated Secretion of Endothelial von Willebrand Factor Is Accompanied by Rapid Redistribution to the Cell Surface of the Intracellular Granule Membrane Protein GMP–140" *J. Bio. Chem.,* 264(14):7768–7771 (1989).
Holguin, et al., *J. Clin. Invest.,* 84:7–17 (1989).
Husler, et al., "Chimeras of Human Complement C9 Reveal the site Recognized by Complement Regulatory Protein CD59", *J. Biol. Chem.,* 270(8):3438–3486 (1995).
Husler, et al., "Role of a Disulfide–bonded Peptide Loop within Human Complement C9 in the species–Selectivity of Complement Inhibitor CD59",*Biochem.,* 35(10):3263–3269 (1996).
Itakura, et al., in *Ann. Rev. Biochem.,* 1984 53:323–356 (1984).
Inai, et al.,*Histochemistry* (German), 99(5):335–362 (1993).
Kabat, et al., Sequences of Proteins of Immunlogical Interest, 4th Ed. (U.S. Dept. Health and Human Services, Bethesda, MD, 1987).
Lewis & Dean, *Proc. R. Soc. Lond.,* 236:125–140 and (1989) 141–162.
Lublin & Atkinson,*Current Topics Microbio. Immunol.,* 153:123–145 (1989).
Maher, et al., (1989).
McKinaly & Rossman, *Annu. Rev. Pharmacol. Toxicol.,* 29:111–122 (1989).
Medof, et al., *J. Exp. Med.* 160:1558–1578 (1984).
Merrifield, *J. Am. Chem. Soc.,* 85:2149–2154 (1964).
Mulder, et al., *Hum. Immunol.,* 36(3):186–192 (1993).
Narang, et al., in Methods Enzymol., 65:610–620 (1980).
Ninomiya & Sims, "Contribution of the N–Linked Carbohydrate of Erythrocyte Antigen CD59 to Its Complement–inhibitory Activity ", *J. Biol. Chem.,* 267(12):8404–8410 (1992).
Ninomiya & Sims, "The Human Complement Regulatory Protein CD59 Binds to the α–Chain of C8 and to the Domain of C9", *J. Bio. Chem.* , 267(19):13675–13680 (1992).

(List continued on next page.)

Primary Examiner—Lila Feisee
Assistant Examiner—Susan Ungar
Attorney, Agent, or Firm—Arnall Golden & Gregory, LLP

[57]  ABSTRACT

Pharmaceutical compositions are designed based on the criticality of a portion of C9 for assembly of the C5b9 complex, which specifically modulate binding of CD59 to C9, either molecules structurally mimicking C9 amino acid residues 359 to 384 which bind to CD59 or molecules binding to C9 amino acid residues 359 to 384. Molecules which inhibit CD59 binding include peptides containing residues 359–384 which compete for binding with the other components of the C5b9 complex and anti-idiotypic antibodies immunoreactive with C9 amino acid residues 359 to 384. Molecules which prevent assembly of the C5b-9 complex include antibodies and antibody fragments immunoreactive with amino acid residues 359 to 384 of C9, peptides that bind to amino acid residues 359 to 384 of C9, and nucleotide molecules that bind to amino acid residues 359 to 384 of C9.

4 Claims, 4 Drawing Sheets

OTHER PUBLICATIONS

Offensperger, et al., *EMBO J.,* 12:1257–1262 (1993).

Perry & Davies, *QSAR: Quantitative Structure–Activity Relationships in Drug Design* pp. 189–193 (Alan R. Liss, inc. 1989).

Ripka, New Scientist, 54–57 (Jun. 16, 1988).

Rollins, et al., "Inhibition of Homologous Complement by CD59 is Mediated by a Species–Selective Recognition Conferred Through Binding to C8 Within C5b–8 or C9 Within C5b–9[1]", J. Immunol., 146:2345–2351 (1991).

Rollins & Sims, "The Complement–Inhibitory Activity of CD59 Resides In Its Capacity to Block Incorporation of C9 Into Membrane C5b–9 [1]",*J. Immunol.,* 144:3478–3483 (1990).

Rotivinen, et al.,*Acta Pharmaceutica Fennica,*97:159–166 (198).

Sambrook, et al., Chapters 5, 6) to purely synthetic methods for example, by the cyanoethy phosphoramidite method using a Milligen or Beckman System 1Plus DNA synthesizer.

Sarin, et al., *Proc. Natl. Acad. Sci. USA,* 85:7448–7794 (1989).

Schaller, et al. *J. Protein Chem.,* 13:472–473 (1994).

Schonermark, et al. *,J. Immunol.,* 136:1772–1776 (1986).

Shaw, et al.,*Nucleic Acids Res,* 19:747–750 (1991).

Sims, "Interaction of Human Platelets with the Complement System ",*Platelet Immunobiology,* Chapter 18, 354–383 (1990).

Sims, et al., "Regulatory Control of Complement on Blood Platelets, " *J. Biol. Chem.,* 264:19228–19235 (1989).

Stauber, et al., *J. Immunol. Methods* (Netherlands), 161(2):157–168 (1993).

Sugita, et al., *J. Biochem.*(Tokyo), 104:633–637 (1988).

Szostak,*TIBS,*19:89 (1992).

Venkateswaran, et al.,*Hybridoma,*11(6)729–739 (1992).

Wiedmer & Sims, "Cyanine Dye Fluorescence Used to Measure Membrane Potential Changes due to the Assembly of Complement Proteins C5b–9 ", *J. Membr. Biol.,* 84:249–258 (1985).

Wiedmar & Sims, "Effect of Complement Proteins C5b–9 on Blood Platelets ", *J. Bio. Chem.,* 260(13):8014–8019 (1985).

Zalman, et al., *Proc. Natl. Acad. Sci., U.S.A.,*83:6975–6979 (1986).

Burgess et al. (J. Cell Bio. 111:2129–2138) 1990.

Lazar et al (Mol +Cell Bio, 8:1247–1252) 1988.

Tao et al., (J. Immunol, 143:2595–2601 1989.

Stanley et al (EMBO J. 4:375–382, 1985).

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2026 base pairs
        ( B ) TYPE: nucleic acid
        ( C ) STRANDEDNESS: double
        ( D ) TOPOLOGY: linear (ii) MOLECULE TYPE: cDNA (xi) SEQUENCE DESCRIPTION: SEQ ID NO:1:

```
CAGCATGTCA GCCTGCCGGA GCTTTGCAGT TGCAATCTGC ATTTTAGAAA TAAGCATCCT      60
CACAGCACAG TACACGACCA GTTATGACCC AGAGCTAACA GAAAGCAGTG GCTCTGCATC     120
ACACATAGAC TGCAGAATGA GCCCCTGGAG TGAATGGTCA CAATGCGATC CTTGTCTCAG     180
ACAAATGTTT CGTTCAAGAA GCATTGAGGT CTTTGGACAA TTTAATGGGA AAAGATGCAC     240
CGACGCTGTG GGAGACAGAC GACAGTGTGT GCCCACAGAG CCCTGTGAGG ATGCTGAGGA     300
TGACTGCGGA AATGACTTTC AATGCAGTAC AGGCAGATGC ATAAAGATGC GACTTCGGTG     360
TAATGGTGAC AATGACTGCG GAGACTTTTC AGATGAGGAT GATTGTGAAA GTGAGCCCCG     420
TCCCCCCTGC AGAGACAGAG TGGTAGAAGA GTCTGAGCTG GCACGAACAG CAGGCTATGG     480
GATCAACATT TTAGGGATGG ATCCCCTAAG CACACCTTTT GACAATGAGT TCTACAATGG     540
ACTCTGTAAC CGGGATCGGG ATGGAAACAC TCTGACATAC TACCGAAGAC CTTGGAACGT     600
GGCTTCTTTG ATCTATGAAA CCAAAGGCGA GAAAAATTTC AGAACCGAAC ATTACGAAGA     660
ACAAATTGAA GCATTTAAAA GTATCATCCA AGAGAAGACA TCAAATTTTA ATGCAGCTAT     720
ATCTCTAAAA TTTACACCCA CTGAAACAAA TAAAGCTGAA CAATGTTGTG AGGAAACAGC     780
CTCCTCAATT TCTTTACATG GCAAGGGTAG TTTTCGGTTT TCATATTCCA AAAATGAAAC     840
TTACCAACTA TTTTTGTCAT ATTCTTCAAA GAAGGAAAAA ATGTTTCTGC ATGTGAAAGG     900
AGAAATTCAT CTGGGAAGAT TTGTAATGAG AAATCGCGAT GTTGTGCTCA CAACAACTTT     960
TGTGGATGAT ATAAAAGCTT TGCCAACTAC CTATGAAAAG GGAGAATATT TTGCCTTTTT    1020
GGAAACCTAT GGAACTCACT ACAGTAGCTC TGGGTCTCTA GGAGGACTCT ATGAACTAAT    1080
ATATGTTTTG GATAAAGCTT CCATGAAGCG GAAAGGTGTT GAACTAAAAG ACATAAAGAG    1140
ATGCCTTGGG TATCATCTGG ATGTATCTCT GGCTTTCTCT GAAATCTCTG TTGGAGCTGA    1200
ATTTAATAAA GATGATTGTG TAAAGAGGGG AGAGGGTAGA GCTGTAAACA TCACCAGTGA    1260
AAACCTCATA GATGATGTTG TTTCACTCAT AAGAGGTGGA ACCAGAAAAT ATGCATTTGA    1320
ACTGAAAGAA AAGCTTCTCC GAGGAACCGT GATTGATGTG ACTGACTTTG TCAACTGGGC    1380
CTCTTCCATA AATGATGCTC CTGTTCTCAT TAGTCAAAAA CTGTCTCCTA TATATAATCT    1440
GGTTCCAGTG AAAATGAAAA ATGCACACCT AAAGAAACAA AACTTGGAAA GAGCCATTGA    1500
AGACTATATC AATGAATTTA GTGTAAGAAA ATGCCACACA TGCCAAAATG GAGGTACAGT    1560
GATTCTAATG GATGGAAAGT GTTTGTGTGC CTGCCCATTC AAATTTGAGG GAATTGCCTG    1620
TGAAATCAGT AAACAAAAAA TTTCTGAAGG ATTGCCAGCC CTAGAGTTCC CCAATGAAAA    1680
ATAGAGCTGT TGGCTTCTCT GAGCTCCAGT GGAAGAAGAA AACACTAGTA CCTTCAGACT    1740
CCTACCCCTG AAGATAATCT TAGCTGCCAA GTAAATAGCA ACATGCTTCA TGAAAATCCT    1800
ACCAACCTCT GAAGTCTCTT CTCTCTTAGG TCTATAATTT TTTTTTTAAT TTTTCTTCCT    1860
TAAACTCCTG TGATGTTTCC ATTTTTTGTT CCCTAATGAG AAGTCAACAG TGAAATACGC    1920
CAGAACTGCT TTATCCCACG GAAAATGCCA ATCTCTTCTA AAAAAAAACA AAATTAAATT    1980
AAAAACAGAA TGTTGGTTTA AAAAACTTCA AGAAAAAAA AAAAA                      2026
```

(2) INFORMATION FOR SEQ ID NO:2:

(i) SEQUENCE CHARACTERISTICS:
      (A) LENGTH: 2034 base pairs
      (B) TYPE: nucleic acid
      (C) STRANDEDNESS: double
      (D) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| CTCGTGAGCA | GCATGGCCGC | CAGCCACAGC | TTCGCCTTTG | TGGTCTGCGT | TTTAGAAATC | 60 |
| GGTGCCCTGA | CGGCAGGACC | CACTCCCAGC | TATGTCCACG | AGCCGATACA | AAGGAGTGAC | 120 |
| CCTCTGCAGC | CCATAGACTG | CAGGATGAGC | CATGGAGTG | AATGGTCGCA | CTGTGATCCT | 180 |
| TGTCTCAGGC | AAATGTTTCG | TTCAAGGAGC | ATCGAAGTCT | TTGGACAATT | TCATGGGAAA | 240 |
| AGTTGTGTGG | ATGCTCTGGG | CGACAGGCGA | GCGTGTATAC | CTACGGAGGC | ATGCGAAGAC | 300 |
| GCTGAGGAGG | ACTGTGAAAA | AGACGAATTT | CACTGTGGGA | CAGGCAGGTG | CATAAAGAGG | 360 |
| CGACTGCTGT | GTAATGGGGA | CAATGACTGC | GGAGACTTTT | CAGATGAGGA | TGACTGCGAA | 420 |
| ACGGAGCCCC | GTCTTACCTG | TCGCAACCGC | GAGGTCCAAG | AGTCGGAGCT | GGCACGGACA | 480 |
| GCGGGCTATG | GGATCAACAT | TTTAGGGATG | GATCCCCTAG | CCACACCTTT | TGACAACGAG | 540 |
| TACTACCACG | GACTCTGTGA | CCGTGTTTGG | GATGGGAACA | CTTTGACACA | CTATCGAAAA | 600 |
| CCCTGGAATG | TGGCTGTTTT | GGCCTATGAA | ACAAAAATTG | ATAAAAATTT | CAGAACTGAA | 660 |
| TACTATGAAG | AACAGATGCA | GGCATTCAAA | AGTATCATTG | AAGAAGAGAC | ATCAAATTTT | 720 |
| AATGCAAATT | TAGCTCTAAA | ATTTACACCC | ACCGAAGCAA | AAGCAAGTAA | GGCTGAAGAA | 780 |
| GCTTCTCCAA | AAAACAAGTC | TTTGGATGAT | AATGATAAAG | GTTCTCGAG | TAAATTTCAA | 840 |
| TTTTCGTATT | CCAAAAATGA | AACTTACCAA | CTATTCTTGT | CATATTCTTC | ACAGAAGGAA | 900 |
| AAAATGTTTC | TGCTTGTGAA | AGGAATAATT | CAACTGGGAA | GATTTGTGAT | GAAAAATCGG | 960 |
| GGTGTTATGC | TGACAAATAC | CTTCTTGGAT | GATATAAAAT | CTCTGCCAAC | TACCTATGAA | 1020 |
| AAAGGAGAAT | ATTTTGCATT | TTTGGAAACC | TATGGAACCC | ACTATAGTAG | CTCTGGGTCT | 1080 |
| CTGGGAGGAC | GCTATGAGCT | AATTTATGTT | TTGGATAAAG | CTTCCATGAA | GGAGAAAGGG | 1140 |
| ATTGAGCTGA | ATGACATAAA | GAAATGCCTT | GGGTTTGACT | TAGATTTATC | TCTGAATATC | 1200 |
| CCTGGAAAAT | CTGCTGGGCT | TTCGCTCACA | GGACAAGCAA | ATAAAAACAA | TTGCTTAAAG | 1260 |
| AGTGGTCATG | GTAATGCTGT | AAACATCACC | AGGGCTAACC | TCATAGATGA | TGTGATTTCA | 1320 |
| CTCATAAGAG | GAGGAACCCA | AAAATTTGCG | TTTGAATTGA | AAGAAAAGCT | TCTCACCAAA | 1380 |
| GCCAAGATGG | TTGACGTGAC | GGACTTTATC | AATTGGGCCT | CTTCCTTAAG | TGATGCTCCA | 1440 |
| GTGCTCATCA | ATCAAAAACT | GTCCCCTATA | TATAATCTGA | TTCCTGTGAA | AATAAAAGAT | 1500 |
| GCGCACCAAA | AGAGACAGAA | TCTGGAGAGA | GGAATTGAAG | ATTACATCAA | TGAATTCAGC | 1560 |
| ACGAAAAAGT | GCTCCCCCTG | CCAAAACGGA | GGCACTGCAC | TTCTGATGGA | TGGCCAGTGT | 1620 |
| TTGTGTACCT | GCCCGTTTAT | GTTCGAGGGG | ATTGCCTGTG | AAATCTCCAA | ACGAAAACTG | 1680 |
| GCTTAAGGAT | TGCCAGCCCC | CACCCCCACC | CCCAAAATG | CAACTGTTGA | GTTCCCTGAG | 1740 |
| CTCAAATGGA | AGAAAAACAA | CACCAGGACC | TTCAATGTA | AGATCCTGCC | CTGCCTGGAG | 1800 |
| ATAGTCCTTG | CTGGCACATG | AAAAGCAACA | TGTTTCATGA | AAACCCTACC | AACCTCTGAA | 1860 |
| GCCTCGCTCT | CTCTCTGGTC | TGCAATGCCT | GTTTTCCCC | ATAAACCCCT | GTAATGTTTC | 1920 |
| CATTTTTATT | TAATGAAGAG | ACAGCCATGA | GCTGTGCCAG | AAGTGTTTTC | TCCCACAGCC | 1980 |
| AATGCCAGCC | TCTTGCTAAT | AAAAGAAAAT | AAAATTCAAA | AAAAAAAAAA | AAAA | 2034 |

( 2 ) INFORMATION FOR SEQ ID NO:3:

( i ) SEQUENCE CHARACTERISTICS:
( A ) LENGTH: 82 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:3:

| Leu | Tyr | Glu | Leu | Ile | Tyr | Val | Leu | Asp | Lys | Ala | Ser | Met | Lys | Arg | Lys |
|---|---|---|---|---|---|---|---|---|---|---|---|---|---|---|---|
| 1 | | | | 5 | | | | | 10 | | | | | | 15 |
| Gly | Val | Glu | Leu | Lys | Asp | Ile | Lys | Arg | Cys | Leu | Gly | Tyr | His | Leu | Asp |
| | | | 20 | | | | | 25 | | | | | 30 | | |
| Val | Ser | Leu | Ala | Phe | Ser | Glu | Ile | Ser | Val | Gly | Ala | Glu | Phe | Asn | Lys |
| | | 35 | | | | | 40 | | | | | 45 | | | |
| Asp | Asp | Cys | Val | Lys | Arg | Gly | Glu | Gly | Arg | Ala | Val | Asn | Ile | Thr | Ser |
| | 50 | | | | | 55 | | | | | 60 | | | | |
| Glu | Asn | Leu | Ile | Asp | Asp | Val | Val | Ser | Leu | Ile | Arg | Gly | Gly | Thr | Arg |
| 65 | | | | 70 | | | | | 75 | | | | | | 80 |
| Lys | Tyr | | | | | | | | | | | | | | |

(2) INFORMATION FOR SEQ ID NO:4:

(i) SEQUENCE CHARACTERISTICS:
(A) LENGTH: 86 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

| Arg | Tyr | Glu | Leu | Ile | Tyr | Val | Leu | Asp | Lys | Ala | Ser | Met | Lys | Glu | Lys |
|---|---|---|---|---|---|---|---|---|---|---|---|---|---|---|---|
| 1 | | | | 5 | | | | | 10 | | | | | | 15 |
| Gly | Ile | Glu | Leu | Asn | Asp | Ile | Lys | Lys | Cys | Leu | Gly | Phe | Asp | Leu | Asp |
| | | | 20 | | | | | 25 | | | | | 30 | | |
| Leu | Ser | Leu | Asn | Ile | Pro | Gly | Lys | Ser | Ala | Gly | Leu | Ser | Leu | Thr | Gly |
| | | 35 | | | | | 40 | | | | | 45 | | | |
| Gln | Ala | Asn | Lys | Asn | Asn | Cys | Leu | Lys | Ser | Gly | His | Gly | Asn | Ala | Val |
| | 50 | | | | | 55 | | | | | 60 | | | | |
| Asn | Ile | Thr | Arg | Ala | Asn | Leu | Ile | Asp | Asp | Val | Ile | Ser | Leu | Ile | Arg |
| 65 | | | | 70 | | | | | 75 | | | | | | 80 |
| Gly | Gly | Thr | Gln | Lys | Phe | | | | | | | | | | |
| | | | | 85 | | | | | | | | | | | |

(2) INFORMATION FOR SEQ ID NO:5:

(i) SEQUENCE CHARACTERISTICS:
(A) LENGTH: 560 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

| Ser | Met | Ser | Ala | Cys | Arg | Ser | Phe | Ala | Val | Ala | Ile | Cys | Ile | Leu | Glu |
|---|---|---|---|---|---|---|---|---|---|---|---|---|---|---|---|
| 1 | | | | 5 | | | | | 10 | | | | | | 15 |
| Ile | Ser | Ile | Leu | Thr | Ala | Gln | Tyr | Thr | Thr | Ser | Tyr | Asp | Pro | Glu | Leu |
| | | | 20 | | | | | 25 | | | | | 30 | | |
| Thr | Glu | Ser | Ser | Gly | Ser | Ala | Ser | His | Ile | Asp | Cys | Arg | Met | Ser | Pro |
| | | 35 | | | | | 40 | | | | | 45 | | | |
| Trp | Ser | Glu | Trp | Ser | Gln | Cys | Asp | Pro | Cys | Leu | Arg | Gln | Met | Phe | Arg |
| | 50 | | | | | 55 | | | | | 60 | | | | |
| Ser | Arg | Ser | Ile | Glu | Val | Phe | Gly | Gln | Phe | Asn | Gly | Lys | Arg | Cys | Thr |

-continued

|  | 65 |  |  |  |  | 70 |  |  |  |  | 75 |  |  |  |  | 80 |
|---|---|---|---|---|---|---|---|---|---|---|---|---|---|---|---|---|

Asp Ala Val Gly Asp Arg Arg Gln Cys Val Pro Thr Glu Pro Cys Glu
                85                   90                  95

Asp Ala Glu Asp Asp Cys Gly Asn Asp Phe Gln Cys Ser Thr Gly Arg
            100            105            110

Cys Ile Lys Met Arg Leu Arg Cys Asn Gly Asp Asn Asp Cys Gly Asp
    115             120            125

Phe Ser Asp Glu Asp Asp Cys Glu Ser Glu Pro Arg Pro Pro Cys Arg
   130           135            140

Asp Arg Val Val Glu Glu Ser Glu Leu Ala Arg Thr Ala Gly Tyr Gly
145               150            155              160

Ile Asn Ile Leu Gly Met Asp Pro Leu Ser Thr Pro Phe Asp Asn Glu
            165            170            175

Phe Tyr Asn Gly Leu Cys Asn Arg Asp Arg Asp Gly Asn Thr Leu Thr
         180            185            190

Tyr Tyr Arg Arg Pro Trp Asn Val Ala Ser Leu Ile Tyr Glu Thr Lys
       195            200            205

Gly Glu Lys Asn Phe Arg Thr Glu His Tyr Glu Glu Gln Ile Glu Ala
   210           215            220

Phe Lys Ser Ile Ile Gln Glu Lys Thr Ser Asn Phe Asn Ala Ala Ile
225               230            235              240

Ser Leu Lys Phe Thr Pro Thr Glu Thr Asn Lys Ala Glu Gln Cys Cys
         245            250            255

Glu Glu Thr Ala Ser Ser Ile Ser Leu His Gly Lys Gly Ser Phe Arg
       260            265            270

Phe Ser Tyr Ser Lys Asn Glu Thr Tyr Gln Leu Phe Leu Ser Tyr Ser
     275            280            285

Ser Lys Lys Glu Lys Met Phe Leu His Val Lys Gly Glu Ile His Leu
   290           295            300

Gly Arg Phe Val Met Arg Asn Arg Asp Val Val Leu Thr Thr Thr Phe
305               310            315              320

Val Asp Asp Ile Lys Ala Leu Pro Thr Thr Tyr Glu Lys Gly Glu Tyr
         325            330            335

Phe Ala Phe Leu Glu Thr Tyr Gly Thr His Tyr Ser Ser Ser Gly Ser
       340            345            350

Leu Gly Gly Leu Tyr Glu Leu Ile Tyr Val Leu Asp Lys Ala Ser Met
     355            360            365

Lys Arg Lys Gly Val Glu Leu Lys Asp Ile Lys Arg Cys Leu Gly Tyr
   370           375            380

His Leu Asp Val Ser Leu Ala Phe Ser Glu Ile Ser Val Gly Ala Glu
385               390            395              400

Phe Asn Lys Asp Asp Cys Val Lys Arg Gly Glu Gly Arg Ala Val Asn
         405            410            415

Ile Thr Ser Glu Asn Leu Ile Asp Asp Val Val Ser Leu Ile Arg Gly
       420            425            430

Gly Thr Arg Lys Tyr Ala Phe Glu Leu Lys Glu Lys Leu Leu Arg Gly
     435            440            445

Thr Val Ile Asp Val Thr Asp Phe Val Asn Trp Ala Ser Ser Ile Asn
   450           455            460

Asp Ala Pro Val Leu Ile Ser Gln Lys Leu Ser Pro Ile Tyr Asn Leu
465               470            475              480

Val Pro Val Lys Met Lys Asn Ala His Leu Lys Lys Gln Asn Leu Glu
         485            490            495

```
Arg  Ala  Ile  Glu  Asp  Tyr  Ile  Asn  Glu  Phe  Ser  Val  Arg  Lys  Cys  His
          500                     505                    510

Thr  Cys  Gln  Asn  Gly  Gly  Thr  Val  Ile  Leu  Met  Asp  Gly  Lys  Cys  Leu
          515                     520                    525

Cys  Ala  Cys  Pro  Phe  Lys  Phe  Glu  Gly  Ile  Ala  Cys  Glu  Ile  Ser  Lys
          530                     535                    540

Gln  Lys  Ile  Ser  Glu  Gly  Leu  Pro  Ala  Leu  Glu  Phe  Pro  Asn  Glu  Lys
545                      550                     555                         560
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ser  Cys  Trp  Leu  Leu
1                    5
```

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala  Pro  Val  Glu  Glu  Glu  Asn  Thr  Ser  Thr  Phe  Arg  Leu  Leu  Pro  Leu
1                   5                     10                         15
Lys  Ile  Ile  Leu  Ala  Ala  Lys
                    20
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ile  Ala  Thr  Cys  Phe  Met  Lys  Ile  Leu  Pro  Thr  Ser  Glu  Val  Ser  Ser
1                   5                     10                         15
Leu  Leu  Gly  Leu
               20
```

(2) INFORMATION FOR SEQ ID NO:9:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Phe  Phe  Phe
```

(2) INFORMATION FOR SEQ ID NO:10:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Phe Phe Phe Leu Lys Leu Leu
1               5

(2) INFORMATION FOR SEQ ID NO:11:

(i) SEQUENCE CHARACTERISTICS:
(A) LENGTH: 51 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Cys Phe His Phe Leu Phe Pro Asn Glu Lys Ser Thr Val Lys Tyr Ala
1               5                   10                  15

Arg Thr Ala Leu Ser His Gly Lys Cys Gln Ser Leu Leu Lys Lys Asn
            20                  25                  30

Lys Ile Lys Leu Lys Thr Glu Cys Trp Phe Lys Lys Leu Gln Arg Lys
            35                  40                  45

Lys Lys Lys
        50

(2) INFORMATION FOR SEQ ID NO:12:

(i) SEQUENCE CHARACTERISTICS:
(A) LENGTH: 561 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Leu Val Ser Ser Met Ala Ala Ser His Ser Phe Ala Phe Val Val Cys
1               5                   10                  15

Val Leu Glu Ile Gly Ala Leu Thr Ala Gly Pro Thr Pro Ser Tyr Val
            20                  25                  30

His Glu Pro Ile Gln Arg Ser Asp Pro Leu Gln Pro Ile Asp Cys Arg
            35                  40                  45

Met Ser Pro Trp Ser Glu Trp Ser His Cys Asp Pro Cys Leu Arg Gln
        50              55                  60

Met Phe Arg Ser Arg Ser Ile Glu Val Phe Gly Gln Phe His Gly Lys
65                      70                  75                  80

Ser Cys Val Asp Ala Leu Gly Asp Arg Arg Ala Cys Ile Pro Thr Glu
                85                  90                  95

Ala Cys Glu Asp Ala Glu Glu Asp Cys Glu Lys Asp Glu Phe His Cys
            100                 105                 110

Gly Thr Gly Arg Cys Ile Lys Arg Arg Leu Leu Cys Asn Gly Asp Asn
            115                 120                 125

```
Asp Cys Gly Asp Phe Ser Asp Glu Asp Cys Glu Thr Glu Pro Arg
    130                 135                 140
Leu Thr Cys Arg Asn Arg Glu Val Gln Glu Ser Glu Leu Ala Arg Thr
145             150                 155                 160
Ala Gly Tyr Gly Ile Asn Ile Leu Gly Met Asp Pro Leu Ala Thr Pro
                165                 170                 175
Phe Asp Asn Glu Tyr Tyr His Gly Leu Cys Asp Arg Val Trp Asp Gly
            180                 185                 190
Asn Thr Leu Thr His Tyr Arg Lys Pro Trp Asn Val Ala Val Leu Ala
        195                 200                 205
Tyr Glu Thr Lys Ile Asp Lys Asn Phe Arg Thr Glu Tyr Tyr Glu Glu
    210                 215                 220
Gln Met Gln Ala Phe Lys Ser Ile Ile Glu Glu Thr Ser Asn Phe
225                 230                 235                 240
Asn Ala Asn Leu Ala Leu Lys Phe Thr Pro Thr Glu Ala Lys Ala Ser
                245                 250                 255
Lys Ala Glu Glu Ala Ser Pro Lys Asn Lys Ser Leu Asp Asp Asn Asp
            260                 265                 270
Lys Gly Phe Ser Ser Lys Phe Gln Phe Ser Tyr Ser Lys Asn Glu Thr
            275                 280                 285
Tyr Gln Leu Phe Leu Ser Tyr Ser Ser Gln Lys Glu Lys Met Phe Leu
    290                 295                 300
Leu Val Lys Gly Ile Ile Gln Leu Gly Arg Phe Val Met Lys Asn Arg
305                 310                 315                 320
Gly Val Met Leu Thr Asn Thr Phe Leu Asp Asp Ile Lys Ser Leu Pro
                325                 330                 335
Thr Thr Tyr Glu Lys Gly Glu Tyr Phe Ala Phe Leu Glu Thr Tyr Gly
            340                 345                 350
Thr His Tyr Ser Ser Ser Gly Ser Leu Gly Gly Arg Tyr Glu Leu Ile
        355                 360                 365
Tyr Val Leu Asp Lys Ala Ser Met Lys Glu Lys Gly Ile Glu Leu Asn
    370                 375                 380
Asp Ile Lys Lys Cys Leu Gly Phe Asp Leu Asp Leu Ser Leu Asn Ile
385                 390                 395                 400
Pro Gly Lys Ser Ala Gly Leu Ser Leu Thr Gly Gln Ala Asn Lys Asn
                405                 410                 415
Asn Cys Leu Lys Ser Gly His Gly Asn Ala Val Asn Ile Thr Arg Ala
            420                 425                 430
Asn Leu Ile Asp Asp Val Ile Ser Leu Ile Arg Gly Gly Thr Gln Lys
        435                 440                 445
Phe Ala Phe Glu Leu Lys Glu Lys Leu Leu Thr Lys Ala Lys Met Val
    450                 455                 460
Asp Val Thr Asp Phe Ile Asn Trp Ala Ser Ser Leu Ser Asp Ala Pro
465                 470                 475                 480
Val Leu Ile Asn Gln Lys Leu Ser Pro Ile Tyr Asn Leu Ile Pro Val
                485                 490                 495
Lys Ile Lys Asp Ala His Gln Lys Arg Gln Asn Leu Glu Arg Gly Ile
            500                 505                 510
Glu Asp Tyr Ile Asn Glu Phe Ser Thr Lys Lys Cys Ser Pro Cys Gln
        515                 520                 525
Asn Gly Gly Thr Ala Leu Leu Met Asp Gly Gln Cys Leu Cys Thr Cys
    530                 535                 540
Pro Phe Met Phe Glu Gly Ile Ala Cys Glu Ile Ser Lys Arg Lys Leu
545                 550                 555                 560
```

Ala ( 2 ) INFORMATION FOR SEQ ID NO:13:

( i ) SEQUENCE CHARACTERISTICS:
       ( A ) LENGTH: 44 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:13:

```
Gly Leu Pro Ala Pro Thr Pro Thr Pro Gln Asn Ala Thr Val Glu Phe
 1               5                  10                  15

Pro Glu Leu Lys Trp Lys Lys Asn Asn Thr Arg Thr Phe Gln Cys Lys
                20                  25                  30

Ile Leu Pro Cys Leu Glu Ile Val Leu Ala Gly Thr
                35                  40
```

( 2 ) INFORMATION FOR SEQ ID NO:14:

( i ) SEQUENCE CHARACTERISTICS:
       ( A ) LENGTH: 30 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:14:

```
Lys Ala Thr Cys Phe Met Lys Thr Leu Pro Thr Ser Glu Ala Ser Leu
 1               5                  10                  15

Ser Leu Trp Ser Ala Met Pro Val Phe Pro His Lys Pro Leu
                20                  25                  30
```

( 2 ) INFORMATION FOR SEQ ID NO:15:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:15:

```
Cys Phe His Phe Tyr Leu Met Lys Arg Gln Pro
 1               5                  10
```

( 2 ) INFORMATION FOR SEQ ID NO:16:

( i ) SEQUENCE CHARACTERISTICS:
       ( A ) LENGTH: 28 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:16:

```
Ala Val Pro Glu Val Phe Ser Pro Thr Ala Asn Ala Ser Leu Leu Leu
 1               5                  10                  15

Ile Lys Glu Asn Lys Ile Gln Lys Lys Lys Lys
                20                  25
```

C9 COMPLEMENT INHIBITOR

The present invention is generally in the area of inhibitors of complement-mediated inflammation, and is specifically directed to a compound inhibiting assembly of the C5b9 complex.

The U.S. government has certain rights in this invention by virtue of grant HL 36061 from the Heart, Lung and Blood Institute, National Institutes of Health to Peter J. Sims.

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in normal serum of man and other vertebrates.

The classic complement pathway involves an initial antibody recognition of, and binding to, an antigenic site (SA) on a target cell. This surface bound antibody subsequently reacts with the first component of complement, C1q, forming a C1-antibody complex with Ca ++, C1r, and C1s which is proteolytically active. C1s cleaves C2 and C4 into active components, C2a and C4a. The C4b, 2a complex is an active protease called C3 convertase, and acts to cleave C3 into C3a and C3b. C3b forms a complex with C4b, 2a to produce C4b, 2a, 3b, which cleaves C5 into C5a and C5b. C5b combines with C6. The C5b, 6 complex combines with C7 to form the ternary complex C5b, 6, 7. The C5b, 6, 7 complex binds C8 at the surface of the cell, which may develop functional membrane lesions and undergo slow lysis. Upon binding of C9 to the C8 molecules in the C5b, 6, 7, 8 complex, lysis of bacteria and other foreign cells is rapidly accelerated.

The C5b-9 proteins of the human plasma complement system have been implicated in non-lytic stimulatory responses from certain human vascular and blood cells. The capacity of C5b-9 to modify membrane permeability and to selectively alter ion conductance is thought to elicit these non-lytic responses from human cells. In the case of human blood platelets and vascular endothelium, assembly of the C5b-9 complex initiates a transient and reversible depolarization of the plasma membrane potential, a rise in cytosolic Ca2+, metabolic conversion of arachidonate to thromboxane or prostacyclin, and the activation of intracellular protein kinases. In addition, human platelets exposed to C5b-9 undergo shape changes, secretory fusion of intracellular storage granules with plasma membrane, and the vesiculation of membrane components from the cell surface. Human endothelial cells exposed to the human C5b-9 proteins secrete high molecular weight multimers of the platelet adhesion protein, von Willibrand Factor (vWF), and the intracellular granule membrane protein, GMP140, is translocated from the Weibel-Palade body to the endothelial surface. High molecular weight multimers of vWF have been implicated in the pathogenesis of vaso-occlusive platelet adherence to endothelium and cell surface GMP140 has been implicated in the adherence of inflammatory leukocytes to endothelium.

These effects of complement proteins C5b-9 on platelet and endothelial cells alter the normal regulation of the enzymes of the plasma coagulation system at these cell surfaces. For example, the generation of platelet membrane microparticles by vesiculation is accompanied by the exposure of membrane binding sites for coagulation factor Va. Binding of factor Va to the platelet plasma membrane and to these membrane microparticle sites initiates assembly of the prothrombinase enzyme complex. This complex in turn accelerates coagulation factor Xa activation of prothrombin to thrombin which promotes plasma clotting. Similarly, C5b-9 binding to the endothelial cell results in the exposure of plasma membrane receptors for the prothrombinase complex, thereby accelerating the generation of thrombin from prothrombin at the endothelial surface.

This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

Assembly of the C5b-9 complex is normally limited in plasma by the amount of C5b generated by proteolysis of C5 to its biologically-active fragments C5b and C5a. In addition to plasmin and other plasma or cell-derived proteases, two enzymes of the complement system can cleave C5 to C5a and C5b, the membrane-stabilized enzyme complexes C4b2a and C3bBb (C5-convertases). The activity of these two enzymes is normally inhibited on the surface of human blood and vascular membranes by the plasma membrane proteins, "membrane cofactor protein" (CD46), described by Lublin and Atkinson, *Current Topics Microbiol. Immunol.* 153:123 (1989) and "decay-accelerating factor" (CD55), Medof, et al., *J. Exp. Med.* 160:1558 (1984).

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets and b) local intravascular complement activation resulting in membrane deposition of C5b-9 complexes accompanies coronary vessel occlusion and may affect the ultimate extent of myocardial damage associated with infarction.

There is now considerable evidence that the human erythrocyte membrane as well as the plasma membranes of other human blood cells and vascular endothelium are normally protected from these effects of complement by cell-surface proteins that specifically inhibit activation of the C5b-9 pore upon C9 binding to membrane C5b-8, as reported by Holguin, M. H., et al., *J. Clin. Invest.* 84, 7–17 (1989); Sims, P. J., et al., *J. Biol. Chem.* 264, 19228–19235 (1989); Davies, A., et al., *J. Exp. Med.* 170, 637–654 (1989); Rollins, S. A., and Sims, P. J. *J. Immunol.* 144, 3478–3483 (1990); and Hamilton, K. K., et al., *Blood* 76, 2572–2577 (1990). Plasma membrane constituents reported to exhibit this activity include homologous restriction factor (HRF) (C8 -binding protein), as described by Zalman, L. S., et al., *Proc. Natl. Acad. Sci., U.S.A.* 83, 6975–6979 (1986) and Schonermark, S., et al., *J. Immunol.* 136, 1772–1776 (1986), and the leukocyte antigen CD59, described by Sugita, Y., et al., *J. Biochem.* (Tokyo) 104, 633–637 (1988); Holguin, M. H., et al., (1989); Sims, P. J., et al., (1989); Davies, A., (1989); Rollins, S. A., and Sims, P. J. (1990); and Hamilton, K. K., et al., (1990). Accumulated evidence suggest that these two proteins exhibit quite similar properties, including the following: both HRF and CD59 are tethered to the cell surface by a glycolipid anchor, and are deleted from the membranes of the most hemolytically sensitive erythrocytes that arise in the stem cell disorder paroxysmal nocturnal hemoglobinuria; the activity of both inhibitors is species-restricted, showing selectivity for C8 and C9 that are derived from homologous (i.e. human) serum; and both HRF and CD59 appear to function by inhibiting the activation of C9, decreasing the incorporation of C9 into the membrane C5b-9 complex, and limiting propagation of the C9 homopolymer.

In U.S. Pat. No. 5,136,916 to Sims and Wiedmer, Sims and Wiedmer disclose compositions and methods for use thereof relating to polypeptides having the ability to act as an inhibitor of complement C5b-9 complex activity. The compositions contain CD59, active derivatives or fragments thereof which act to inhibit the activity of C5b-9, anti-idiotypic antibodies mimicking the action of the inhibitor proteins or antibodies against C7 or C9 which block the formation of the C5b-9 complex. The compositions can be used in vitro to inhibit C5b-9 related stimulatory responses of platelets and vascular endothelium of perfused organs and tissues, thereby preventing the C5b-9 initiated cell necrosis or stimulated secretion of proteolytic enzymes and the exposure of the procoagulant membrane receptors during collection and in vitro storage. In one variation of this embodiment, the vascular endothelium of organs and tissues to be transplanted are treated with these compositions to protect these cells from complement activation after transplantation. In another embodiment, immune disease states are treated by administering an effective amount of a C5b-9 inhibitor to suppress C5b-9 mediated platelet activation in vivo. Also disclosed are methods for the production of isolated polypeptides that are able to suppress complement C5b-9 mediated platelet and endothelial cell activation.

Human (hu)[1] CD59 antigen is a 18–21 kDa plasma membrane protein that functions as an inhibitor of the C5b-9 membrane attack complex (MAC) of hu complement. CD59 interacts with both the C8 and C9 components of MAC during its assembly at the cell surface, thereby inhibiting formation of the membrane-inserted C9 homopolymer responsible for MAC cytolytic activity. This serves to protect hu blood and vascular cells from injury arising through activation of complement in plasma. CD59's inhibitory activity is dependent upon the species of origin of C8 and C9, with greatest inhibitory activity observed when C9 is from hu or other primates. By contrast, CD59 exerts little or no inhibitory activity towards C8 or C9 of most other species, including rabbit (rb). Because the activity of CD59 is largely restricted to regulating hu C9, and the activity of analogous complement inhibitors expressed by cells of other species is likewise generally selective for homologous C9, xenotypic cells and tissue are particularly susceptible to complement-mediated destruction due to unregulated activity of MAC. This phenomenon underlies hyperacute immune rejection after xenotransplantation.

Analysis of the physical association of CD59 with components of MAC suggested that separate binding sites for cD59 are contained within the α-chain of hu C8 and within hu C9. Within C9, this site(s) has been mapped to between residues 334–415. The complement-inhibitory activity of CD59 is species-selective, and is most effective towards C9 derived from human or other primate plasma. The species-selective activity of CD59 was recently used to map the segment of human C9 that is recognized by this MAC inhibitor, using recombinant rabbit/human C9 chimeras that retain lytic function within the MAC [Husler T, Lockert D. H., Kaufman K. M., Sodetz J. M., Sims P. J. (1995). *J. Biol. Chem.* 270:3483–3486]. These experiments suggested that the CD59 recognition domain was contained between residues 334–415 in human C9.

It is apparent that additional or alternative inhibitors of the assembly of the C5b9 complex would be advantageous in inhibition of complement mediated inflammation. It is also clear that inhibitors which are extremely specific and which are directed to the most critical regions involved in assembly or function of the complex would be most effective as inhibitors of complement mediated inflammation, with the least likelihood of non-specific side effects.

It is therefore an object of the present invention to provide a method and materials for specifically inhibiting complement mediated inflammation.

It is another object of the present invention to provide a method and materials for determining the species specificity of C9 complement mediated activation and cytolysis.

SUMMARY OF THE INVENTION

CD59 interacts with a segment of human C9 (hu C9) between residues 334–415, immediately C-terminal to the predicted membrane-inserting domain of C9. This segment of C9 contains a region of markedly divergent sequence when hu C9 is compared to C9 of other species, with greatest divergence noted for the peptide segment contained within an internal Cys359–Cys384 disulfide in hu C9. In order to determine whether sequence contained in this peptide loop represents a hu C9-specific motif that is selectively recognized by CD59, CD59's inhibitory activity toward various full-length C9 chimeras containing hu-unique or rabbit (rb)-unique sequence spanning this segment of the C9 polypeptide were analyzed. These experiments revealed that substitution of hu residues 359–391 into otherwise rb C9 yielded a chimera indistinguishable from hu C9 in its regulation by CD59. C9 chimeras generated by substitution of hu C9 sequence flanking either side of residues 359–391 into rb C9 showed no consistent increase in inhibition by CD59. This indicates that only residues contained between 359–391 of hu C9 are directly recognized by CD59. Moreover, truncation of the segment of hu C9 sequence in chimeric rb C9 from 359–391 to the putative recognition loop of hu 359–384 was accompanied by approximately 35% reduction of CD59 inhibitory function. Further, CD59 specifically bound to a synthetic peptide corresponding to residues 359–384 of hu C9. IgG (Fab) specific for the hu C9 359–384 peptide inhibited the hemolytic activity of hu C9 (but not rb C9) in a manner analogous to CD59.

Pharmaceutical compositions are designed based on the criticality of this portion of C9 for assembly of the C5b9 complex which specifically modulate binding of CD59 to C9, either molecules structurally mimicking C9 amino acid residues 359 to 384 which bind to CD59 or molecules binding to C9 amino acid residues 359 to 384. Molecules which inhibit CD59 binding include peptides containing residues 359–384 which compete for binding with the other components of the C5b9 complex and anti-idiotypic antibodies immunoreactive with C9 amino acid residues 359 to 384. Molecules which prevent assembly of the C5b-9 complex include antibodies and antibody fragments immunoreactive with amino acid residues 359 to 384 of C9, peptides that bind to amino acid residues 359 to 384 of C9, and nucleotide molecules that bind to amino acid residues 359 to 384 of C9.

BRIEF DESCRIPTION OF THE DRAWINGS

FIGS. 1A and 1B are a plot of the inhibitory activity of CD59 towards hu/rb chimeras of complement C9. Bar graph (FIG. 1A) summarizes combined results of all experiments measuring the inhibitory activity of CD59 towards recombinant hu/rb chimeras of C9. In each assay, hemolytic titrations of C9 were performed against C5b-8 chE in the presence and absence of membrane CD59, and the percent reduction of hemolysis due to CD59 (ordinate)was determined, with normalization to that observed for hu C9 (100% inhibition). Error bars denote mean +S.D., parentheses indicate number of independent experiments; asterisks (*) indicate significance (p<0.01) when compared to rb C9; pound signs (#) indicate significance (p<0.01) when compared to hu C9. The protein assayed is depicted (FIG. 1B) so as to designate those portions of the polypeptide containing hu C9 (open) or rb C9 (shaded) sequence. Numbers above each construct indicate the junctional hu C9 residue at each transition between hu and rb protein sequence. Bars designated as human C9 and rabbit C9 denote recombinantly-expressed hu and rb C9, respectively. Recombinant C9 chimeras (designated as #1–12) contain human (H) or rabbit (R) sequence according to the deduced mature primary structure of hu and rb C9. In some C9 chimeras, the numbering appears discontinuous because of gaps in the alignment of the hu and rb sequences: 1, R1-338H334-415R425-536; 2, R1-363H359-538; 3, H1-357R 363-536; 4, R1-363H359-415R425-536; 5, R1-363H359-391R401-536; 6, R1-400H392-415R425-536; 7, R1-363H359-384R394-536; 8, H1-333R339-424H416-538; 9, H1-357R363-424H416-538; 10, H1-357R363-400H392-538; 11, H1-391R401-424H416-538; 12, H1-357R363-393H385-538.

FIG. 2 is a schematic representation of the segment of hu C9 identified as containing the CD59 binding site, which according to the proposed domain structure includes: thrombospondin type 1 (TS), LDL-receptor (LDLR), hinge (Hinge), membrane binding (MB), and epidermal growth factor precursor (EGFP) domains. Shaded segment indicates residues 334–415 of hu C9, spanning the putative CD59 binding site. The amino acid sequence of this peptide segment Sequence ID No. 3 is given below, and is shown in an alignment with rb C9 Sequence ID No. 4 (alignment done for full-length polypeptides with the PALIGN program in PCGENE). Asterisks indicate sequence identity. Dotted lines indicate the Cys 359/384 disulfide of hu C9 and the assumed corresponding internal disulfide in rb C9. Residue numbers refer to the mature proteins.

FIG. 3 is a graph showing inhibitory activity of CD59 is unaffected by disruption of the Cys 359/384 disulfide. Recombinant hu C9 was expressed with a Cys→Ala mutation at either residue 384 or at both residues 359/384, and analyzed as described in FIG. 1. Inhibitory activity of CD59 towards the hemolytic function of each recombinant C9 is expressed as a percentage, relative to that measure for wild-type hu C9 (ordinate). Error bars denote mean +S.D., n, indicates number of independent experiments; asterisks indicate significance (p,0.001) compared to hu C9. Hu C9 and rb C9 denote the wild type hu and rb proteins, respectively.

FIG. 4 is a graph showing CD59 specifically binds hu C9 peptide 359–384. Microplates were coated with hu C9 peptide 359–384 coupled to BSA, and specific binding of biotin-CD59 determined in the presence of affinity-purified antibody against hu C9 residues 359–384 (●), or non-immune IgG (Δ) (IgG concentrations indicated on abscissa). All data were corrected for nonspecific binding of CD59, determined in presence of 20-fold excess of unlabeled CD59. Ordinate denotes absorbance at 405 nm, with correction for nonspecific background. Error bars denote mean +S.D. Data of a single experiment, representative of three so performed.

FIGS. 5A, 5B, 5C and 5D are graphs showing the inhibition of C9 -dependent lysis by antibody against C9-peptide 359–384. Fab of antibody against hu C9 peptide 359–384 (●) was tested for its capacity to inhibit the hemolytic activity of recombinant hu C9 (Figure 5A), hu/rb C9 chimera #7 (FIG. 5B), recombinant rb C9 (FIG. 5C), or hu/rb C9 chimera #12 (FIG. 5D). Residues of human (H) and rabbit (R) sequence in each C9 chimera are indicated in FIG. 1. Also shown is data for non-immune antibody (Δ) (final concentrations indicated on abscissa). In all experiments, C5b-8 chE lacking CD59 served as target cells and hemolysis measured with correction for nonspecific lysis. Data of single experiment, representative of three similar experiments.

DETAILED DESCRIPTION OF THE INVENTION

Figure 1:
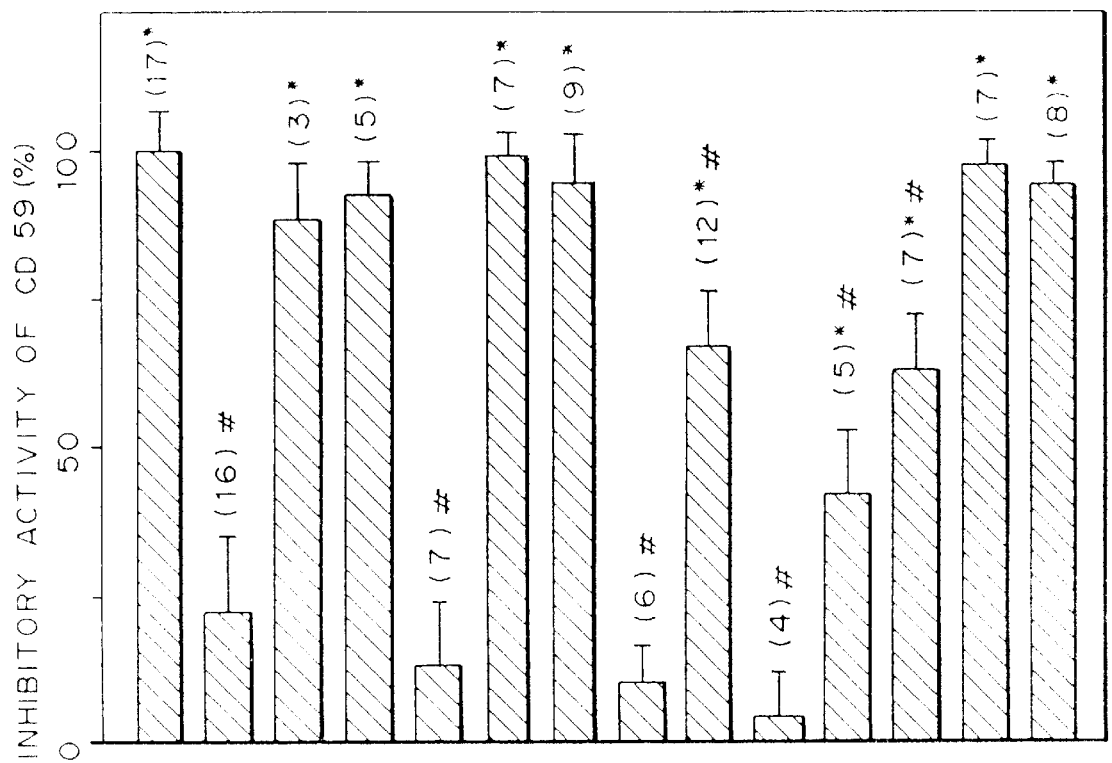
Figure 1:
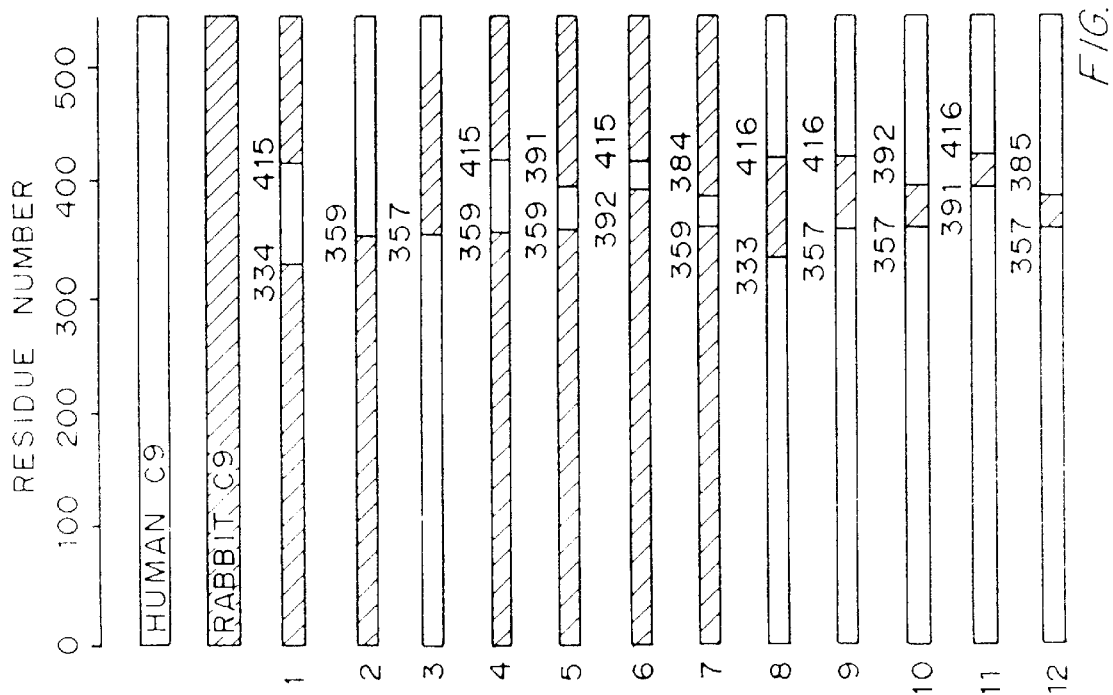

I. C9 Peptide/CD59 C9 binding site Immunomodulators

Peptide sequence in human complement protein C9 has been identified that contributes to the recognition of this protein by its naturally occurring inhibitor, CD59 . CD59 is known to bind to neo-epitopes that become exposed in complement C8 and C9 during assembly of the cytolytic membrane attack complex of proteins C5b through C9. Through this interaction, CD59 interrupts assembly of the C5b-9 complex, protecting the target cell from destruction by these complement proteins. Data demonstrates that antibody raised against this human C9-derived peptide sequence is functionally inhibitory towards the lytic activity of the human C5b-9 complex. This permits design of reagents directed specifically at human C9 that mimic or inhibit the complement-inhibitory function of cell-surface CD59.

Compounds which bind CD59

As demonstrated by the following example, amino acid residues 359–384 of C9 are critical for binding of CD59 to C9, resulting in inhibition of C5b-9 complex assembly. Peptides can be as short as 26 amino acids, less than forty amino acids, or less than 56 amino acids (359 to 415 amino acid peptide fragment of C9). Substitutions based on conserved sequence (rabbit for human, amino acids with similar structure and charge), presence or absence of a disulfide bond between the cysteine residues, and elongation of the peptide through addition of supplemental amino acid sequence, were all shown not to significantly inhibit binding of CD59 to C9. Other derivatives that should also be active include covalently-cyclized derivatives, for example, disulfide-bonded and amide bonded peptides.

The data indicates that CD59 inhibits C9 through binding to hu-specific residues contained within the Cys359–Cys384 disulfide loop of the polypeptide. Optimal interaction of CD59 with this binding site in hu C9 appears to depend upon a few residues located immediately C-terminal to this segment of the protein. Although the specific role of this segment of C9 in membrane attack complex (MAC) assembly is unknown, the data indicates that ligand binding to this site abrogates the lytic activity of the C5b-9 complex, implicating these residues in the conversion of C9 from solution monomer to membrane-embedded polymer. CD59 specifically binds a human C9-derived peptide corresponding to residues 359–384, and antibody (Fab) raised against this C9-derived peptide inhibits the lytic activity of human MAC. Mutant human C9 in which Ala was substituted for Cys 359–384 was found to express normal lytic activity and to be fully inhibited by CD59. This suggests that the intrachain Cys359/Cys384 disulfide bond within C9 is not required to maintain the conformation of this segment of C9 for interaction with CD59. Other substitutions can also be made without decreasing activity.

These compounds are effective as competitive inhibitors of CD59. Other compounds besides the peptides that can be used include anti-idiotypic antibodies and antibody fragments which bind to CD59, nucleotide molecules, and organic molecules that bind to the site on CD59 which binds amino acids 359–384 or 359 to 391. These can be identified using screening and computer assisted design, as described below.

Compounds which Inhibit C5b-9 Assembly

Data demonstrates that antibody raised against this human C9-derived peptide sequence is functionally inhibitory towards the lytic activity of the human C5b-9 complex. Other compounds besides antibodies and antibody fragments which also bind to this peptide portion of C9, thereby preventing assembly of the C5b-9 complex, include peptides, nucleotide molecules, and organic molecules that bind to amino acids 359–384 or 359 to 391. These can be identified using screening and computer assisted design, as described below.

Random generation of binding molecules

Molecules with a given function, catalytic or ligand-binding, can be selected for from a complex mixture of random molecules in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer assisted drug design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, *QSAR: Quantitative Structure-Activity Relationships in Drug Design* pp. 189–193 (Alan R. Liss, Inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Nucleotide molecules which bind either CD59 or the C9 peptide can be generated in vitro, and then inserted into cells. Oligonucleotides can be synthesized on an automated synthesizer (e.g., Model 8700 automated synthesizer of Milligen-Biosearch, Burlington, MA or ABI Model 380B). (see, e.g., Offensperger et. al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620 (1980) (phosphotriester method).

Preparation of Peptides

Proteins can be expressed recombinantly and cleaved by enzymatic digest, expressed from a sequence encoding a peptide, or synthesized using standard techniques. It is a routine matter to make appropriate peptides, test for binding, and then utilize. The peptides can be as short as twenty six amino acids in length and up to 57 amino acids, and are easily prepared by standard techniques. They can also be modified to increase in vivo half-life, by chemical modification of the amino acids or by attachment to a carrier molecule or inert substrate.

The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of C9, or, preferably, by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. No. 4,305, 872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 $\mu$g/kg of body weight. Based on extrapolation from other proteins, for treatment of most inflammatory disorders, the dosage range will be between 0.1 to 70 mg/kg of body weight. This dosage will be dependent, in part, on whether one or more peptides are administered. Based on studies with other peptide fragments blocking binding, the $IC_{50}$, the dose of peptide required to inhibit binding by 50%, ranges from about 50 $\mu$M to about 300 $\mu$M, depending on the peptides. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis.

Antibodies

Antibodies immunoreactive with the C9 peptide or an anti-idiotypic antibody to the antibodies immunoreactive with the C9 peptide can be prepared for use as described above.

In vivo Immunization of Animals

Animals such as mice may be immunized by administration of an amount of immunogen (either the C9 peptide or the antibody to the C9 peptide) effective to produce an immune response. Preferably a mouse is subcutaneously injected in the back with 100 micrograms of antigen, followed three weeks later with an intraperitoneal injection of 100 micrograms of cocaine immunogen with adjuvant, most preferably Freund's complete adjuvant. Additional intraperitoneal injections every two weeks with adjuvant, preferably Freund's incomplete adjuvant, may be necessary until the proper titer in the mouse's blood is achieved. In order to use the mice for fusion and hybridoma production, a titer of at least 1:5000 is preferred, and a titer of 1:100,000 or more is most preferred.

In vitro Immunization

The technique of in vitro immunization of human lymphocytes is frequently employed to generate a large variety of human monoclonal antibodies, since deliberate in vivo priming of humans with many antigens of interest is not feasible until approval by the Food and Drug Administration has been obtained. Techniques for in vitro immunization of human lymphocytes are well known to those skilled in the art. See, e.g., T. Inai, et al., *Histochemistry* (Germany), 99(5):335–362 (May 1993); A. Mulder, et al., *Hum. Immunol.*, 36(3):186–192 (Mar. 1993); H. Harada, et al., *J. Oral Pathol. Med.* (Denmark), 22(4):145–152 (April 1993); N. Stauber, et al., *J. Immunol. Methods* (Netherlands), 161(2): 157–168 (May 26, 1993); and S. Venkateswaran, et al., *Hybridoma*, 11(6):729–739 (Dec. 1992), which are incorporated herein by reference. These techniques can be used to produce antigen-reactive human monoclonal antibodies, including antigen-specific IgG, and IgM human monoclonal antibodies.

Humanization of Antibodies

Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a lesser xenografic rejection stimulus when introduced to a human recipient.

To accomplish humanization of a selected mouse monoclonal antibody, the CDR grafting method described by Daugherty, et al., *Nucl. Acids Res.*, 19:2471–2476 (1991), incorporated herein by reference, may be used. Briefly, the variable region DNA of a selected animal recombinant anti-idiotypic ScFv is sequenced by the method of Clackson, T., et al., *Nature*, 352:624–688, 1991, incorporated herein by reference. Using this sequence, animal CDRs are distinguished from animal framework regions (FR) based on locations of the CDRs in known sequences of animal variable genes. Kabat, H.A., et al., Sequences of Proteins of Immunological Interest, 4th Ed. (U.S. Dept. Health and Human Services, Bethesda, MD, 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

Pharmaceutical Compositions

The compounds described above are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine pp.* 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. No. 4,906,474 4,925,673, and 3,625,214.

II. Methods of treament

The effective amount of composition described above is that which achieves the desired effect: either to inhibit assembly of the C5b-9 complex by binding to C9 or to bind to the endogenous CD59 to prevent the CD59 from inhibiting assembly of the C5b-9 complex, thereby increasing complement mediated activation of cells.

Inhibition of CD59 is useful as an adjuvant for tumor therapy and as a contraceptive since its been demonstrated that CD59 protects sperm from rejection by antibody and complement in the female genital tract and that CD59 expressed on human tumor cells protect those cells from complement mediated lysis.

Inhibition of C5b-9 complex assembly is useful for all disorders characterized by excessive complement activation or complement mediated cytolysis, including, for example, immune disorders and diseases such as immunovasculitis, rheumatoid arthritis, scleroderma, disseminated intravascular coagulation, lupus, paroxysmal nocturnal hemoglobinuria, thrombotic thrombolytic purpura, vascular occlusion, reocclusion after surgery, coronary thrombosis, and myocardial infarction.

The present invention will be further understood by reference to the following studies.

EXAMPLE 1

Demonstration of role of a disulfide bonded peptide loop within hu C9 in the species-selectivity of CD59

EXPERIMENTAL PROCEDURES

Materials

Hu complement proteins C5b6, C7, C8, and C9, and hu erythrocyte membrane glycoprotein CD59 were purified and assayed as described by Davies, et al. *Immunol. Res.* 12, 258–275 (1993), Wiedmer and Sims, *J. Membr. Biol.* 84, 249–258 (1985), and Wiedmer and Sims, *J. Biol. Chem.* 260, 8014–8019 (1985). Hu C9 peptide 359–384 ([allyl-K]-CLGYHLDVSLAFSEISVGAEFNKDD-[allyl-C), BSA-conjugated hu C9 peptide 359–384, and affinity-purified rb IgG against hu C9 peptide 359–384 were custom ordered from Quality Controlled Biochemicals (Hopkinton, Mass.). Full-length cDNA for hu C9 was a generous gift from Dr. J. Tschopp (University of Lausanne, Epalinges, Switzerland) and is described by Dupuis, et al., *Mol. Immunol.* 30, 95–100 (1993), the teachings of which are incorporated herein. Full length cDNA for rb C9 was isolated and cloned into pSVL as reported by Husler, et al., *J. Biol. Chem.* 270, 3483–3486 (1995), the teachings of which are incorporated herein. Chicken erythrocytes (chE) were from Cocalico Biologics, Inc. (Reamstown, Pa.); COS-7 cells were from American Tissue Culture Collection (Rockville, Md.); *E. coli* strain DH5α and Opti-MEM I were from Life Technologies Inc. (Gaithersburg, Md.), Dulbecco's Modified Eagle Medium was from Mediatech Inc. (Herndon, Va.), and heat-inactivated fetal bovine serum was from Biocell (Rancho Dominquez, Calif.). Oligonucleotides were synthesized by the Molecular Biology Core Laboratories, Blood Research Institute.

Solutions

MBS: 150 mM NaCl, 10 mM MOPS, pH7.4; GVBS: 150 mM NaCl, 3.3 mM sodium barbital, 0.15 mM $CaCl_2$, 0.5 mM $MgCl_2$, 0.1%(w/v) gelatin, pH 7.4; GVBE:150 mM NaCl, 3.3 mM sodium barbital, 10 mM EDTA, 0.1%(w/v) gelatin, pH 7.4.

Construction of chimeric C9 cDNA's cDNA's coding for hu/rb C9 chimeras were constructed essentially as described by Husler, et al. (1995). In brief, regions of sequence identity were determined from the aligned sequences of rb and hu C9, and used as junctions for chimeric cDNA construction. Based on these alignments, primers for PCR were designed to generate defined segments of rb and hu C9 cDNA's. Primers annealing to 5'-or 3'-untranslated sequence with added Xbal (5'-end) or Sacl (3'-end) recognition sites were paired with chimeric primers (28–37 bp in length) and used to generate cDNA fragments that contained the desired overlapping sequence at either the 5'-or 3'-ends. These fragments were gel purified, mixed at a 1:1 molar ration, and used in a second amplification with primers located in the 5'-and 3'-untranslated region to produce full length chimeric C9 cDNA's. Fragments were cloned into the Xbal/Sacl sites of pSVL for mammalian expression. PCR fidelity was confirmed by sequencing 3'-coding sequence in each construct, starting from the stop codon and continuing through all junctions of rb and hu sequence. In certain cases, chimeric constructs were further modified by site directed mutagenesis.

Site Directed Mutagenesis

C9 cDNA in pSVL served as a template for site-directed mutagenesis using the Chameleon mutagenesis kit (Stratagene, La Jolla, Calif.). Mutagenesis was performed using 0.25 pmol of template plasmid, 25 pmol of mutagenic primer and 25 pmol of selection primer, the latter chosen to modify SalI, ScaI, or XhoI restriction sites unique to pSVL. The resulting mutagenized plasmids were subject to a minimum of two rounds of selection by restriction digest, and then transformed into E. coli XL1-Blue (Stratagene) for single colony isolation and plasmid purification. In all cases, mutations were confirmed by double stranded sequencing of each purified plasmid.

Transfection of COS-7 cells

Plasmid DNA used in transfections was obtained from purification over Qiagen-tips (Qiagen Inc., Chatsworth, Calif.). COS-7 cells were transfected using DEAE-dextran, then cultured for 24h in Dulbecco's Modified Eagle Medium (Mediatech Inc., Herndon, Va.) supplemented with 10% fetal bovine serum, after which this medium was replaced by Opti-MEM I (Life Technologies, Inc., Gaithersburg, Md.). Cell supernatants were harvested after 48–65h, PMSF (1 mM), benzamidine (1 mM) and EDTA (10 mM) were added and the supernatants concentrated at 4° C. (Centricon 30, Amicon).

Immunoblotting

C9 in the COS-7 supernatants was analyzed by quantitative dot blotting using murine monoclonal antibody P9-2T as described by Husler, et al. (1995).

Biotin-CD59

CD59 was biotinylated by incubation (1 h, room temperature) with a 20-fold molar excess of NHS-LC-biotin in 10 mM MOPS, 0.1% Nonidet P-40, pH 9.0 followed by exhaustive dialysis against charcoal, as described by Chang, et al. J. Biol. Chem. 269, 26424–26430 (1994).

Analysis of the inhibitory function of CD 59 towards recombinant C9 constructs

Hemolytic activity of each C9 construct was assayed using as target cells chE that were reconstituted with purified hu CD59, as described by Husler, et al., (1995). chE were washed extensively and suspended in GVBS, and the membrane C5b67 complex assembled by mixing cells ($1.4 \times 10^9$/ml) with C5b6 (13 µg/ml) followed by addition of C7 (1 µg/ml). After 10 min., the C5b67 chE were diluted to $1.4 \times 10^8$/ml in GVBE and incubated (10 min. 37° C.) with 0 or 750 ng/ml CD59. In each case, the final concentration of Nonidet P-40 was less than 0.002%(v/v). After washing in ice-cold GVBE, $2.8 \times 10^8$ of these cells were incubated (37° C.) in a total volume of 100 µl with 1 ng rb C8 plus 0–50 ng of recombinant C9, serially diluted in Opti-MEM I. Hemolysis was determined after 30 minutes at 37° C., with correction for nonspecific lysis, determined in the absence of C9. In each experiment, the inhibitory activity of CD59 towards each recombinant C9 construct was determined from the reduction in complement lysis of those cells reconstituted with CD59, versus the identically-treated cells omitting CD59, measured at the midpoint of the C9 titration (i.e., 50% hemolysis). In order to directly compare results obtained in experiments performed on different days, data for each recombinant C9 construct were normalized to results obtained in each experiment with hu C9.

CD59 binding to hu C9 peptide 359–384.

The specific binding of CD59 to hu C9-derived peptide 359–384 was measured by microtiter plate assay with biotin-CD59, according to modification of published methods of Chang, et al. (1994) and Husler, et al. (1995). Briefly, the BSA-peptide conjugate was adsorbed to 96 well polyvinyl microplates by overnight coating at 5 µg/ml in 0.1M sodium bicarbonate, pH 8.5. After blocking with 1% (w/v) BSA, wells were washed and incubated (4 hrs., 37° C.) with 0.5–1 , µg/ml biotin-CD59. After washing, the bound biotin-CD59 was detected with Vectsstain™ (Vector Labs, Burlingame, Calif.), developed by addition of p-nitrophenyl phosphate (2 mg/ml) and optical density recorded at 405 nm (VMAXMICROPLATE™ Reader, Molecular Devices, Inc.). In all experiments, correction was made for background adsorption of biotin-CD59 to BSA-coated wells (no peptide) and for nonspecific binding of biotin-CD59 to peptide, determined in the presence of a 20-fold excess of unlabeled CD59. As a positive control for specific binding, comparison was made in each experiment to wells coated with 2 µg/ml hu C9. The capacity of monospecific antibody against hu C9 peptide 359–384 to compete specific binding of CD59 was determined by prior incubation of the BSA-peptide-coated wells with antibody (2 hrs., 0–100 µg/ml LgG) before addition of biotin-CD59.

Inhibition of MAC lysis by antibody against hu C9 peptide 359–384.

The capacity of antibody against hu C9 peptide 359–384 to inhibit MAC was determined by hemolytic assay, using the chE target cells described above, omitting CD59. In these experiments, 0–1 mg/ml Fab of antibody against hu C9 peptide 359–384 (or, non-immune antibody control) was added with recombinant C9 (hu, rb, or chimeric), and complement-specific lysis determined.

RESULTS

C9 chimeras were constructed in which the segment of C9 corresponding to the putative CD59 binding site (residues 334–415 in hu C9; were interchanged between hu and rb C9. These chimeric proteins were then tested for hemolytic activity and for their sensitivity to inhibition by membrane CD59 (FIG. 1A and 1B). Substitution of hu C9 residues 334–415 into rb C9 (chimera #1) resulted in a protein that was indistinguishable from hu C9 in its sensitivity to inhibition by CD59. Conversely, when this same segment of hu C9 was replaced by the corresponding rb C9 sequence (chimera #8), the resulting chimera was indistinguishable from rb C9 and virtually unaffected by the presence of membrane CD59. In these experiments, MAC was assembled using hu C5b67 and rb C8 so as to circumvent known inhibitory interaction of CD59 with hu C8 (Rollins, et al. J. Immunol. 146, 2345–2351 (1991), Ninomiya and Sims J. Biol. Chem. 267, 13675–13680 (1992).

Figure 2:
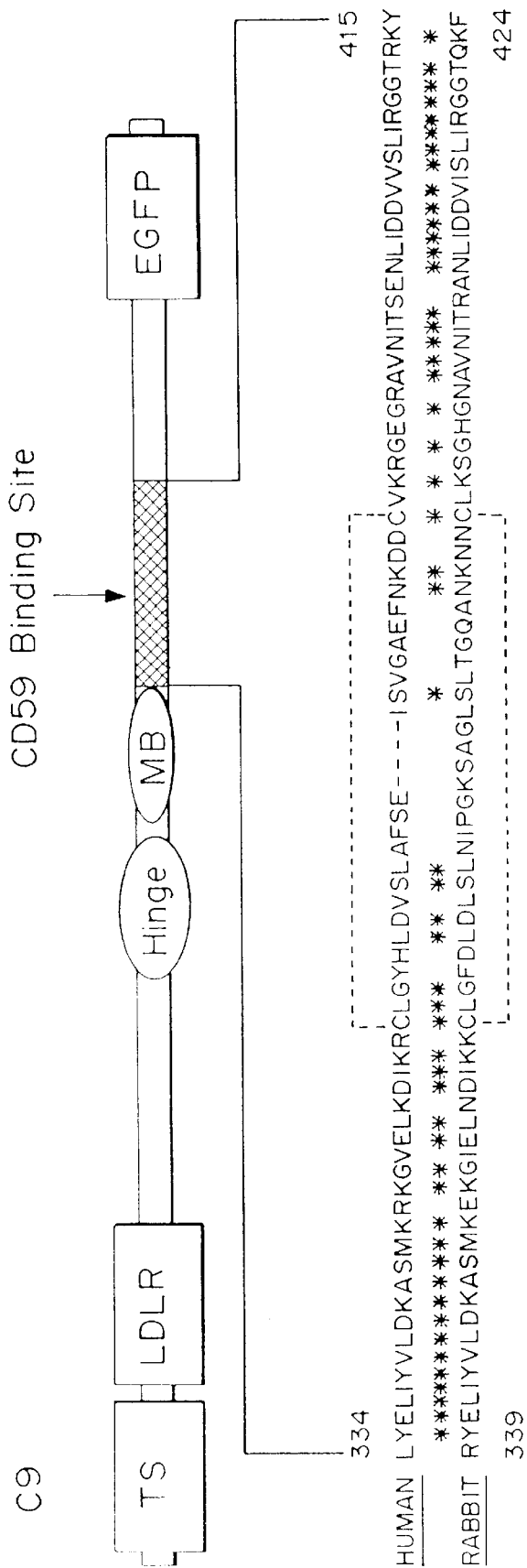

As depicted in FIG. 2, the segment of hu C9 shown to bind CD59 is immediately C-terminal to the putative membrane-spanning domain of the protein, and corresponds to a segment of polypeptide exhibiting particularly low sequence conversation when hu C9 is aligned to C9 of rb or other non-primate species. The most prominent divergence of sequence occurs between two cysteines (Cys359–Cys384 in hu C9) that are conserved in the hu and rb proteins. In hu C9, these cysteines have been shown to form an intrachain disulfide bond (below), as reported by Schaller, et al. J. Protein Chem. 13, 472–473 (1994).

In order to further localize the segment of hu C9 recognized by CD59 and to determine the specific contribution of residues spanning the Cys359/384 disulfide, a series of hu/rb C9 chimeras was constructed by interchanging segments of corresponding hu and rb C9 sequences internal to residues 334–415 . Each of these chimeric proteins was expressed and analyzed for MAC hemolytic function, and for sensitivity to inhibition by membrane CD59. All resulting hu/rb C9 chimeras were functionally active as determined by hemolytic titration against chE containing membrane C5b-8. As shown in FIG. 1, analysis of CD59-inhibitory activity towards each of these proteins revealed inhibition of MAC lytic activity by CD59 was unaffected by replacement of all residues N-terminal to Cys359 of hu C9 with corresponding rb sequence (chimera #2), whereas replacement of all residues C-terminal to residue 358 of hu C9 with corresponding rb sequence (chimera #3) resulted in a protein indistinguishable from rb C9 and only weakly inhibited by CD59. Consistent with the results for chimeras #1–3, substitution of hu C9 residues 359–415 into the corresponding segment of otherwise rb C9 (chimera #4) resulted in a protein that was indistinguishable from hu C9, suggesting that this polypeptide segment of hu C9 (residues 359–415) contains the binding site for CD59.

To further resolve the segment of hu C9 required for species-selective interaction with CD59, additional chimeras were constructed further truncating the segment of hu sequence substituted into rb C9 (chimera #5–7). Data for these chimeras revealed that whereas hu residues 359–391 conferred full recognition by CD59 (chimera #5), hu C9 residues 392–415 failed to confer any recognition by CD59 (chimera #5), hu C9 residues 392–415 failed to confer any recognition by CD59 when inserted into an otherwise rb C9 (chimera #6). Truncation of the inserted segment of hu C9 sequence from 359–391 (chimera #5) to 359–384 (chimera #7) was accompanied by a small but significant reduction in inhibition of MAC lytic activity by CD59. These results imply that CD59 directly interacts with the segment of hu C9 contained between residues 359–391, with the peptide segment spanning the intrachain Cys359/384 disulfide substantially contributing to this interaction.

CD59's interaction with hu C9 was abrogated by replacement of sequence spanning this putative CD59 recognition domain with corresponding rb sequence (chimeras #8–12). Replacement of hu C9 residues 334–415 with corresponding rb sequence (chimera #8) completely eliminated hu-selective interaction with CD59, as anticipated for results obtained for the complementary construct, chimera #1. Nevertheless, when the segment of rb-derived sequence substituted into otherwise hu C9 was further truncated, the resulting chimeras (chimeras #9–12) retained a surprising degree of sensitivity to the inhibitory effects of CD59, characteristic of hu C9. Thus substitution of rb sequence for the residues internal to Cys359–384 of hu C9 (chimera #12) did not significantly diminish CD59's capacity to inhibit the lytic activity of C9, while C-terminal extension of the segment of rb sequence to residue 415 (chimera #9) did not completely eliminate interaction with CD59. Taken together with results for chimeras #1–5, these data indicate that whereas hu C9 residues 359–391 alone are sufficient to confer recognition by CD59, segments of the polypeptide immediately flanking this segment significantly contribute to the extent to which this binding site is expressed.

Figure 3:
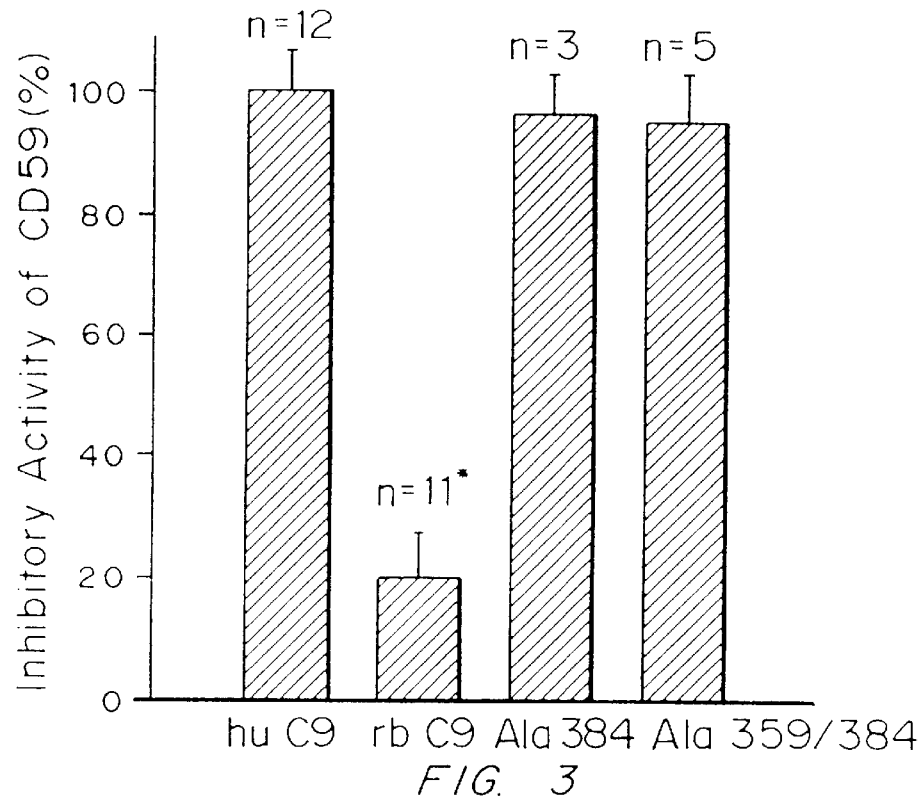

The Cys359/384 disulfide in hu C9 has recently been reported to be highly labile and subject to spontaneous reduction in the native protein, as reported Hatanaka, et al., Biochim. Biophys. Acta Protein Struct. Mol. Enzymol. 1209, 117–122 (1994). Since the data suggested that residues internal to Cys359/384 contribute in-large-part to species-selective recognition by CD59, the extent to which the CD59 recognition site in C9 is affected by disruption of this bond was examined. Mutant hu C9 was expressed with Ala substitutions at Cys359 and Cys384 and tested for hemolytic activity and for sensitivity to inhibition by CD59. As revealed by data of FIG. 3, disruption of this disulfide bond did not significantly affect the hemolytic activity of the protein nor the capacity of CD59 to specifically inhibit C9 lytic activity. This suggests that the segment of hu C9 forming the CD59 binding site is either conformationally constrained independent of the Cys359–384 disulfide, or, that this binding site is expressed in the primary structure of hu C9, independent of protein folding.

Figure 4:
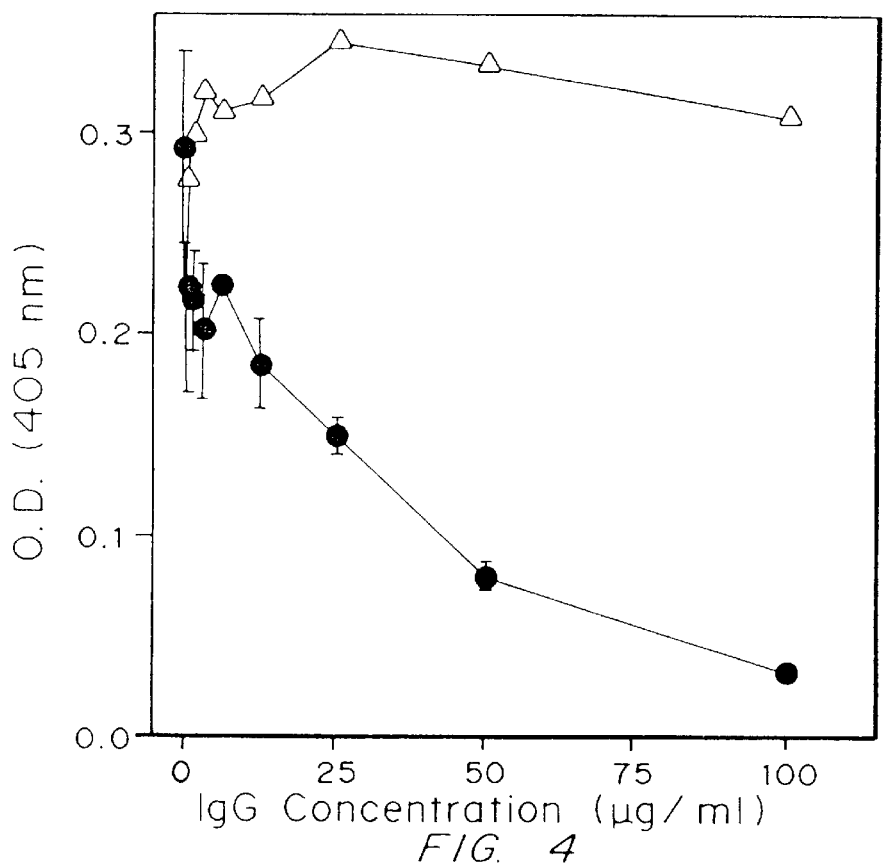

In order to confirm that the peptide segment spanning hu C9 359–384 can itself mediate interaction with CD59, this 26 residue peptide was synthesized, coupled to BSA, and analyzed for CD59 binding, using biotin-CD59 conjugate in a micro plate assay. As demonstrated by FIG. 4, biotin-CD59 specifically bound to C9 peptide 359–384, inhibited binding was inhibited by excess unlabeled CD59 or by antibody directed against the peptide.

Figure 5A:
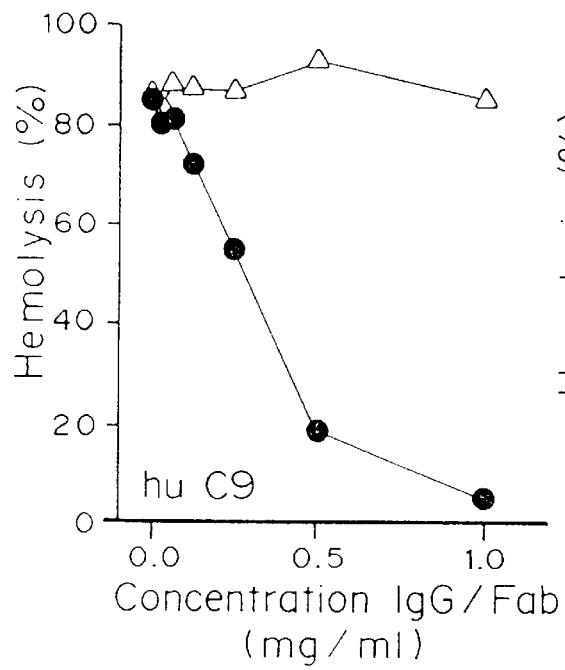
Figure 5B:
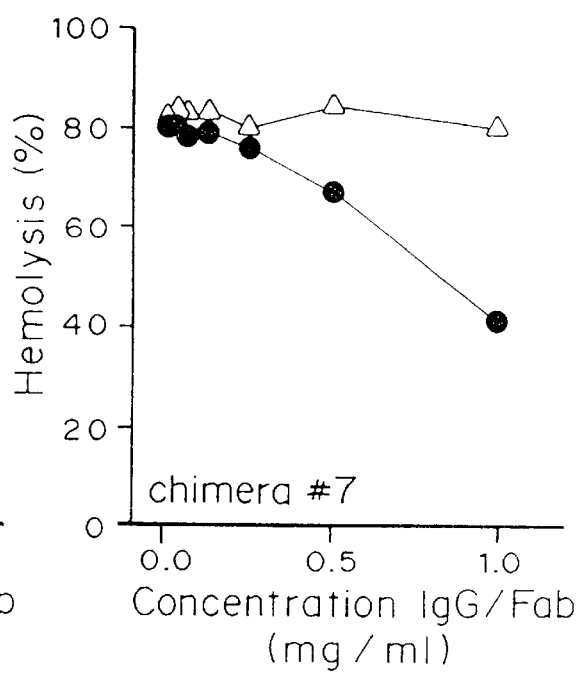
Figure 5C:
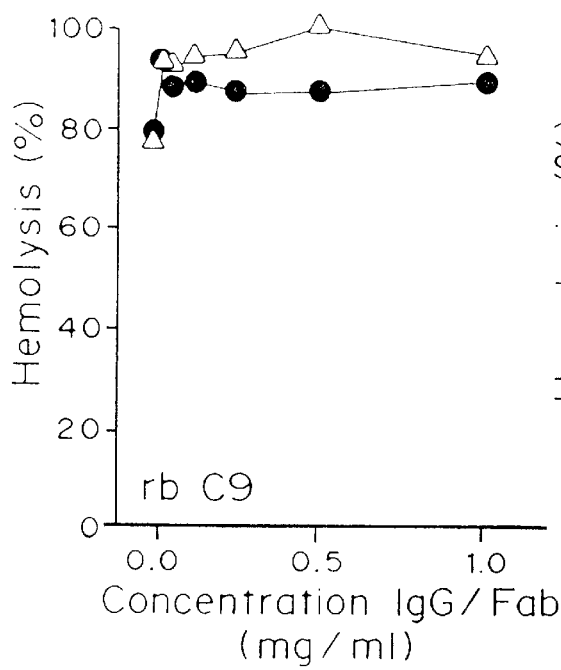
Figure 5D:
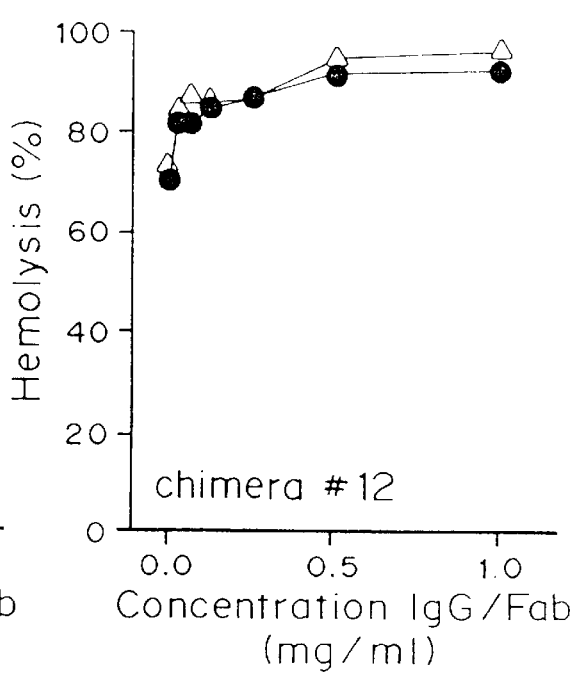

CD59 is known to bind to C9 after C9 incorporates into the C5b-9 complex, and through this interaction inhibit propagation of membrane-inserted C9 polymer, limiting lytic activity of MAC. In order to confirm the importance of the peptide segment recognized by CD59 to MAC assembly, Fab of antibody raised against the hu C9 peptide 359–384 was tested for its capacity to inhibit the hemolytic activity of the hu C5b-9 complex, under the same condition used to evaluate the inhibitory function of CD59. As shown by the data of FIGS. 5 A–D, this Fab inhibited hemolytic activity of hu C9 (FIG. 5A) and C9 chimera #7 (representing rb C9 containing hu C9 residues 359–384, FIG. 1, FIG. 5B), but had no effect on the hemolytic activity of either rb C9 (FIG. 5C) or chimera #12 (representing substitution of the corresponding segment of rb C9 residues into hu C9; FIG. 1, FIG. 5D).

The experiments show that hu C9 residues 359–391 promote CD59 binding, and that this segment of hu C9 contributes to the species-selective regulation of MAC function, providing an initial clue to the structural motif(s) through which this inhibitor selectively regulates the lytic activity of hu C5b-9 complex. These data further indicate that the capacity of CD59 to optimally interact with this segment of hu C9 is significantly influenced by residues immediately C-terminal to this segment of the C9 polypeptide.

Whereas the data establish that residues internal to Cys359–Cys384 contribute to recognition by CD59, the disulfide bond between these two Cys is apparently not required either for maintenance of C9's hemolytic activity within MAC, or, for normal regulation of that activity by membrane CD59. These conclusions derived by Cys/Ala mutagenesis in recombinant hu C9 (FIG. 3) are consistent with previous reports indicating: (i) the intrinsic liability of the Cys 359–384 disulfide in C9 purified from hu plasma, where spontaneous reduction of this bond did not appear to alter C9 hemolytic activity, and (ii) that a specific CD59 binding site is retained in reduced and carboxymethylated hu C9, in hu C9-derived peptide fragments, and can be demonstrated for E. coli fusion proteins contains hu C9-derived sequence spanning residues 359–384. This suggests that the CD59 binding site expressed by this segment of hu C9 reflects interactions between amino acid side chains that do not require formation of the Cys 359/Cys384 disulfide bond.

As noted above, chimeras generated by substituting limited segments of hu C9 into rb C9 revealed that the segment of hu C9 between 359–384 uniquely conferred recognition by CD59, and that this interaction was enhanced by C-terminal extension of hu sequence to residue 391 (cf. Chimeras #1–7; FIG. 1). Surprisingly, chimeras generated by replacing these same segments of hu C9 with corresponding rb C9 sequence did not exhibit a complementary decrease in interaction with CD59, except when the segment of rb-derived sequence replaced in hu C9 residues spanning 334–415 (cf. Chimeras #8–12; FIG. 1).

Modifications and variations will be obvious to those skilled in the art from the foregoing detailed description. Such modifications and variations are intended to come within the scope of the following claims.

```
**************************************************
* TRANSLATION OF A NUCLEIC ACID SEQUENCE *
**************************************************

Done on DNA sequence HUMC9.

DE  HUMAN COMPLEMENT COMPONENT OF MRNA, COMPLETE CDS.
OS  HOMO SAPIENS

Total number of bases is: 2026.
Analysis done on the complete sequence.
Done on (absolute) phase(s): 2.
Using the Universal genetic code.

10                  20                  30                  40
                 |                   |                   |                   |
CAG CAT GTC AGC CTG CCG GAG CTT TGC AGT TGC AAT CTG CAT TTT
 S   M   S   A   C   R   S   F   A   V   A   I   C   I   L 50                  60                  70                  80                  90
         |                   |                   |                   |                   |
AGA AAT AAG CAT CCT CAC AGC ACA GTA CAC GAC CAG TTA TGA CCC
 E   I   S   I   L   T   A   Q   Y   T   T   S   Y   D   P 100                 110                 120                 130
                 |                   |                   |                   |
AGA GCT AAC AGA AAG CAG TGG CTC TGC ATC ACA CAT AGA CTG CAG
 E   L   T   E   S   S   G   S   A   S   H   I   D   C   R 140                 150                 160                 170                 180
         |                   |                   |                   |                   |
AAT GAG CCC CTG GAG TGA ATG GTC ACA ATG CGA TCC TTG TCT CAG
 M   S   P   W   S   E   W   S   Q   C   D   P   C   L   R 190                 200                 210                 220
                 |                   |                   |                   |
ACA AAT GTT TCG TTC AAG AAG CAT TGA GGT CTT TGG ACA ATT TAA
 Q   M   F   R   S   R   S   I   E   V   F   G   Q   F   N 230                 240                 250                 260                 270
         |                   |                   |                   |                   |
TGG GAA AAG ATG CAC CGA CGC TGT GGG AGA CAG ACG ACA GTG TGT
 G   K   R   C   T   D   A   V   G   D   R   R   Q   C   V 280                 290                 300                 310
                 |                   |                   |                   |
GCC CAC AGA GCC CTG TGA GGA TGC TGA GGA TGA CTG CGG AAA TGA
 P   T   E   P   C   E   D   A   E   D   D   C   G   N   D 320                 330                 340                 350                 360
         |                   |                   |                   |                   |
CTT TCA ATG CAG TAC AGG CAG ATG CAT AAA GAT GCG ACT TCG GTG
 F   Q   C   S   T   G   R   C   I   K   M   R   L   R   C 370                 380                 390                 400
                 |                   |                   |                   |
TAA TGG TGA CAA TGA CTG CGG AGA CTT TTC AGA TGA GGA TGA TTG
 N   G   D   N   D   C   G   D   F   S   D   E   D   D   C 410                 420                 430                 440                 450
         |                   |                   |                   |                   |
TGA AAG TGA GCC CCG TCC CCC CTG CAG AGA CAG AGT GGT AGA AGA
 E   S   E   P   R   P   P   C   R   D   R   V   V   E   E 460                 470                             490
                 |                   |             480                 |
GTC TGA GCT GGC ACG AAC AGC AGG CTA TGG GAT CAA CAT TTT AGG
 S   E   L   A   R   T   A   G   Y       I   N   I   L   G 500                 510                 520                 530                 540
         |                   |                   |                   |                   |
GAT GGA TCC CCT AAG CAC ACC TTT TGA CAA TGA GTT CTA CAA TGG
 M   D   P   L   S   T   P   F   D   N   E   F   Y   N   G 550                 560                 570                 580
                 |                   |                   |                   |
ACT CTG TAA CCG GGA TCG GGA TGG AAA CAC TCT GAC ATA CTA CCG
 L   C   N   R   D   R   D   G   N   T   L   T   Y   Y   R 590                 600                 610                 620                 630
         |                   |                   |                   |                   |
AAG ACC TTG GAA CGT GGC TTC TTT GAT CTA TGA AAC CAA AGG CGA
 R   P   W   N   V   A   S   L   I   Y   E   T   K   G   E
```

-continued

```
         640               650               660               670
          |                 |                 |                 |
GAA AAA TTT CAG AAC CGA ACA TTA CGA AGA ACA AAT TGA AGC ATT
 K   N   F   Q   N   R   T   L   R   R   T   N   *   S   I
     680               690               700               710               720
      |                 |                 |                 |                 |
TAA AAG TAT CAT CCA AGA GAA GAC ATC AAA TTT TAA TGC AGC TAT
 *   K   Y   H   P   R   E   D   I   K   F   *   C   S   Y 730               740               750               760
          |                 |                 |                 |
ATC TCT AAA ATT TAC ACC CAC TGA AAC AAA TAA AGC TGA ACA ATG
 I   S   K   I   Y   T   H   *   N   K   *   S   *   T   M 770               780               790               800               810
      |                 |                 |                 |                 |
TTG TGA GGA AAC AGC CTC CTC AAT TTC TTT ACA TGG CAA GGG TAG
 L   *   G   N   S   L   L   N   F   F   T   W   Q   G   *

820               830               840               850
          |                 |                 |                 |
TTT TCG GTT TTC ATA TTC CAA AAA TGA AAC TTA CCA ACT ATT TTT
 F   S   V   F   I   F   Q   K   *   N   L   P   T   I   F 860               870               880               890               900
      |                 |                 |                 |                 |
GTC ARA TTC TTC AAA GAA GGA AAA AAT GTT TCT GCA TGT GAA AGG
 V   X   F   F   K   E   G   K   N   V   S   A   C   E   R 910               920               930               940
          |                 |                 |                 |
AGA AAT TCA TCT GGG AAG ATT TGT AAT GAG AAA TCG CGA TGT TGT
 R   N   S   S   G   K   I   C   N   E   K   S   R   C   C 950               960               970               980               990
      |                 |                 |                 |                 |
GCT CAC AAC AAC TTT TGT GGA TGA TAT AAA AGC TTT GCC AAC TAC
 A   H   N   N   F   C   G   *   Y   K   S   F   A   N   Y 1000              1010              1020              1030
          |                 |                 |                 |
CTA TGA AAA GGG AGA ATA TTT TGC CTT TTT GGA AAC CTA TGG AAC
 L   *   K   G   R   I   F   C   L   F   G   N   L   W   N 1040              1050              1060              1070              1080
      |                 |                 |                 |                 |
TCA CTA CAG TAG CTC TGG GTC TCT AGG AGG ACT CTA TGA ACT AAT
 S   L   Q   *   L   W   V   S   R   R   T   L   *   T   N 1090              1100              1110              1120
          |                 |                 |                 |
ATA TGT TTT GGA TAA AGC TTC CAT GAA GCG AAA AGG TGT TGA ACT
 I   C   F   G   *   S   F   H   E   A   K   R   C   *   T 1130              1140              1150              1160              1170
      |                 |                 |                 |                 |
AAA AGA CAT AAA GAG ATG CCT TGG TAT CAT CTG GAT GTA TCT CTT
 K   R   H   K   E   M   P   W   Y   H   L   D   V   S   L 1180              1190              1200              1210
          |                 |                 |                 |
GGC TTT CTC TGA AAT CTC TGT TGG AGC TGA ATT AAT AAA GAT GA
 G   F   L   *   N   L   C   W   S   *   I   N   K   D   D 1220              1230              1240              1250              1260
      |                 |                 |                 |                 |
TTG TGT AAA GAG GGG AGA GGG TAG AGC TGT AAA CAT CAC CAG TGA
 L   C   K   E   G   R   G   *   S   C   K   H   H   Q   *

1270              1280              1290              1300
          |                 |                 |                 |
AAA CCT CAT AGA TGA TGT TGT TTC ACT CAT AAG AGG TGG AAC CAG
 K   P   H   R   *   C   C   F   T   H   K   R   W   N   Q 1310              1320              1330              1340              1350
      |                 |                 |                 |                 |
AAA ATA TGC ATT TGA ACT GAA AGA AAA GCT TCT CCG AGG AAC CGT
 K   I   C   I   *   T   E   R   K   A   S   P   R   N   R 1360              1370              1380              1390
          |                 |                 |                 |
GAT TGA TGT GAC TGA CTT TGT CAA CTG GGC CTC TTC CAT AAA TGA
 D   *   C   D   *   L   C   Q   L   G   L   F   H   K   *
```

```
              1400            1410            1420            1430            1440
               |               |               |               |               |
      TGC TCC TGT TCT CAT TAG TCA AAA ACT GTC TCC TAT ATA TAA TCT
       A   P   V   L   I   S   Q   K   L   S   P   I   Y   N   L 1450            1460            1470            1480
                       |               |               |               |
      GGT TCC AGT GAA AAT GAA AAA TGC ACA CCT AAA GAA ACA AAA CTT
       V   P   V   K   M   K   N   A   H   L   K   K   Q   N   L 1490            1500            1510            1520            1530
               |               |               |               |               |
      GGA AAG AGC CAT TGA AGA CTA TAT CAA TGA ATT TAG TGT AAG AAA
       E   R   A   I   E   D   Y   I   N   E   F   S   V   R   K
                      1540            1550            1560            1570
                       |               |               |               |
      ATG CCA CAC ATG CCA AAA TGG AGG TAC AGT GAT TCT AAT GGA TGG
       C   H   T   C   Q   N   G   G   T   V   I   L   M   D   G 1580            1590            1600            1610            1620
               |               |               |               |               |
      AAA GTG TTT GTG TGC CTG CCC ATT CAA ATT TGA GGG AAT TGC CTG
       K   C   L   C   A   C   P   F   K   F   E   G   I   A   C 1630            1640            1650            1660
                       |               |               |               |
      TGA AAT CAG TAA ACA AAA AAT TTC TGA AGG ATT GCC AGC CCT AGA
       E   I   S   K   Q   K   I   S   E   G   L   P   A   L   E 1670            1680            1690            1700            1710
               |               |               |               |               |
      GTT CCC CAA TGA AAA ATA GAG CTG TTG GCT TCT CTG AGC TCC AGT
       F   P   N   E   K   -   S   C   W   L   L   -   A   P   V 1720            1730            1740            1750
                       |               |               |               |
      GGA AGA AGA AAA CAC TAG TAC CTT CAG ACT CCT ACC CCT GAA GAT
       E   E   E   N   T   S   T   F   R   L   L   P   L   K   I 1760            1770            1780            1790            1800
               |               |               |               |               |
      AAT CTT AGC TGC CAA GTA AAT AGC AAC ATG CTT CAT GAA AAT CCT
       I   L   A   K   -   I   A   T   C   F   M   K   I   L 1810            1820            1830            1840
                       |               |               |               |
      ACC AAC CTC TGA AGT CTC TTC TCT CTT AGG TCT ATA ATT TTT TTT
       P   T   S   E   V   S   S   L   L   G   L   -   F   F   F 1850            1860            1870            1880            1890
               |               |               |               |               |
      TTA ATT TTT CCT CCT TAA ACT CCT GTG ATG TTT CCA TTT TTT GTT
       -   F   F   F   L   K   L   L   -   C   F   H   F   L   F 1900            1910            1920            1930
                       |               |               |               |
      CCC TAA TGA GAA GTC AAC AGT GAA ATA CGC CAG AAC TGC TTT ATC
       P   N   E   K   S   T   V   K   Y   A   R   T   A   L   S 1940            1950            1960            1970            1980
               |               |               |               |               |
      CCA CGG AAA ATG CCA ATC TCT TCT AAA AAA AAA CAA AAT TAA ATT
       H   G   K   C   Q   S   L   L   K   K   N   K   I   K   L 1990            2000            2010            2020
                       |               |               |               |
      AAA AAC AGA ATG TTG GTT TAA AAA ACT TCA AAG AAA AAA AAA AAA
       K   T   E   C   W   F   K   K   L   Q   R   K   K   K   K
      A
```

****************************************************
\* TRANSLATION OF A NUCLEIC ACID SEQUENCE \*
****************************************************

Done on DNA sequence RC9GENBANK.

DE  RABBIT C9 CLONE#15, SEQUENCE CORRECTION 1-13-95, 2 BP AFTER STOP
DE  CODON DELETED, 1-17-95 ECORI ADAPTOR SEQUENCE DELETED

Total number of bases is: 2034.
Analysis done on the complete sequence.

-continued

Done on (absolute) phase(s): 1.
Using the Universal genetic code.

```
              10              20              30              40
              |               |               |               |
CTC GTG AGC AGC ATG GCC GCC AGC CAC AGC TTC GCC TTT GTG GTC
 L   V   S   S   M   A   A   S   H   S   F   A   F   V   V 50              60              70              80              90
         |               |               |               |               |
TGC GTT TTA GAA ATC GGT GCC CTG ACG GCA GGA CCC ACT CCC AGC
 C   V   L   E   I   G   A   L   T   A   G   P   T   P   S 100             110             120             130
              |               |               |               |
TAT GTC CAC GAG CCG ATA CAA AGG AGT GAC CCT CTG CAG CCC ATA
 Y   V   H   E   P   I   Q   R   S   D   P   L   Q   P   I 140             150             160             170             180
          |               |               |               |               |
GAC TGC AGG ATG AGC CCA TGG AGT GAA TGG TCG CAC TGT GAT CCT
 D   C   R   M   S   P   W   S   E   W   S   H   C   D   P 190             200             210             220
              |               |               |               |
TGT CTC AGG CAA ATG TTT CGT TCA AGG AGC ATC GAA GTC TTT GGA
 C   L   R   Q   M   F   R   S   R   S   I   E   V   F   G 230             240             250             260             270
          |               |               |               |               |
CAA TTT CAT GGG AAA AGT TGT GTG GAT GCT CTG GGC GAC AGG CGA
 Q   F   H   G   K   S   C   V   D   A   L   G   D   R   R 280             290             300             310
              |               |               |               |
GCG TGT ATA CCT ACG GAG GCA TGC GAA GAC GCT GAG GAG GAC TGT
 A   C   I   P   T   E   A   C   E   D   A   E   E   D   C 320             330             340             350             360
          |               |               |               |               |
GAA AAA GAC GAA TTT CAC TGT GGG ACA GGC AGG TGC ATA AAG AGG
 E   K   D   E   F   H   C   G   T   G   R   C   I   K   R 370             380             390             400
              |               |               |               |
CGA CTG CTG TGT AAT GGG GAC AAT GAC TGC GGA GAC TTT TCA GAT
 R   L   L   C   N   G   D   N   D   C   G   D   F   S   D 410             420             430             440             450
          |               |               |               |               |
GAG GAT GAC TGC GGA ACG GAG CCC CGT CTT ACC TGT CGC AAC CGC
 E   D   D   C   E   T   E   P   R   L   T   C   R   N   R 460             470             480             490
              |               |               |               |
GAG GTC CAA GAG TCG GAG CTG GCA CGG ACA GCG GGC TAT GGG ATC
 E   V   Q   E   S   E   L   A   R   T   A   G   Y   G   I 500             510             520             530             540
          |               |               |               |               |
AAC ATT TTA GGG ATG GAT CCC CTA GCC ACA CCT TTT GAC AAC GAG
 N   I   L   G   M   D   P   L   A   T   P   F   D   N   E 550             560             570             580
              |               |               |               |
TAC TAC CAC GGA CTC TGT GAC CGT GTT TGG GAT GGG AAC ACT TTG
 Y   Y   H   G   L   C   D   R   V   W   D   G   N   T   L 590             600             610             620             630
          |               |               |               |               |
ACA CAC TAT CGA AAA CCC TGG AAT GTG GCT GTT TTG GCC TAT GAA
 T   H   Y   R   K   P   W   N   V   A   V   L   A   Y   E 640             650             660             670
              |               |               |               |
ACA AAA ATT GAT AAA AAT TTC AGA ACT GAA TAC TAT GAA GAA CAG
 T   K   I   D   K   N   F   R   T   E   Y   Y   E   E   Q 680             690             700             710             720
          |               |               |               |               |
ATG CAG GCA TTC AAA AGT ATC ATT GAA GAA GAG ACA TGA AAT TTT
 M   Q   A   F   K   S   I   I   E   E   E   T   *   N   F
```

-continued

```
       730             740             750             760
        |               |               |               |
AAT GCA AAT TTA GCT CTA AAA TTT ACA CCC ACC GAA GCA AAA GCA
 N   A   N   L   A   L   K   F   T   P   T   E   A   K   A 770             780             790             800             810
        |               |               |               |               |
AGT AAG GCT GAA GAA GCT TCT CCA AAA AAC AAG TCT TTG GAT GAT
 S   K   A   E   E   A   S   P   K   N   K   S   L   D   D 820             830             840             850
        |               |               |               |
AAT GAT AAA GGT TTC TCG AGT AAA TTT CAA TTT TCG TAT TCC AAA
 N   D   K   G   F   S   S   K   F   Q   F   S   Y   S   K 860             870             880             890             900
        |               |               |               |               |
AAT GAA ACT TAC CAA CTA TTC TTG TCA TAT TCT TCA CAG AAG GAA
 N   E   T   Y   Q   L   F   L   S   Y   S   S   Q   K   E 910             920             930             940
        |               |               |               |
AAA ATG TTT CTG CTT GTG AAA GGA ATA ATT CAA CTG GGA AGA TTT
 K   M   F   L   L   V   K   G   I   I   Q   L   G   R   F 950             960             970             980             990
        |               |               |               |               |
GTG ATG AAA AAT CGG GGT GTT ATG CTG ACA AAT ACC TTC TTG GAT
 V   M   K   N   R   G   V   M   L   T   N   T   F   L   D 1000            1010            1020            1030
        |               |               |               |
GAT ATA AAA TCT CTG CCA ACT ACC TAT GAA AAA GGA GAA TAT TTT
 D   I   K   S   L   P   T   T   Y   E   K   G   E   Y   F 1040            1050            1060            1070            1080
        |               |               |               |               |
GCA TTT TTG GAA ACC TAT GGA ACC CAC TAT AGT AGC TCT GGG TCT
 A   F   L   E   T   Y   G   T   H   Y   S   S   S   G   S 1090            1100            1110            1120
        |               |               |               |
CTG GGA GGA CGC TAT GAG CTA ATT TAT GTT TTG GAT AAA GCT TCC
 L   G   G   R   Y   E   L   I   Y   V   L   D   K   A   S 1130            1140            1150            1160            1170
        |               |               |               |               |
ATG AAG GAG AAA GGG ATT GAG CTG AAT GAC ATA AAG AAA TGC CTT
 M   K   E   K   G   I   E   L   N   D   I   K   K   C   L 1180            1190            1200            1210
        |               |               |               |
GGG TTT GAC TTA GAT TTA TCT CTG AAT ATC CCT GGA AAA TCT GCT
 G   F   D   L   D   L   S   L   N   I   P   G   K   S   A 1220            1230            1240            1250            1260
        |               |               |               |               |
GGG CTT TCG CTC ACA GGA CAA GCA AAT AAA AAC AAT TGC TTA AAG
 G   L   S   L   T   G   Q   A   N   K   N   N   C   L   K 1270            1280            1290            1300
        |               |               |               |
AGT GGT CAT GGT AAT GCT GTA AAC ATC ACC AGG GCT AAC CTC ATA
 S   G   H   G   N   A   V   N   I   T   R   A   N   L   I 1310            1320            1330            1340            1350
        |               |               |               |               |
GAT GAT GTG ATT TCA CTC ATA AGA GGA GGA ACC CAA AAA TTT GCG
 D   D   V   I   S   L   I   R   G   G   T   Q   K   F   A 1360            1370            1380            1390
        |               |               |               |
TTT GAA TTG AAA GAA AAG CTT CTC ACC AAA GCC AAG ATG GTT GAC
 F   E   L   K   E   K   L   L   T   K   A   K   M   V   D 1400            1410            1420            1430            1440
        |               |               |               |               |
GTG ACG GAC TTT ATC AAT TGG GCC TCT TCC TTA AGT GAT GCT CCA
 V   T   D   F   I   N   W   A   S   S   L   S   D   A   P 1450            1460            1470            1480
        |               |               |               |
GTG CTC ATC AAT CAA AAA CTG TCC CCT ATA TAT AAT CTG ATT CCT
 V   L   I   N   Q   K   L   S   P   I   Y   N   L   I   P
```

-continued

```
      1490             1500             1510             1520             1530
       |                |                |                |                |
GTG AAA ATA AAA GAT GCG CAC CAA AAG AGA CAG AAT CTG GAG AGA
 V   K   I   K   D   A   H   Q   K   R   Q   N   L   E   R 1540             1550             1560             1570
                |                |                |                |
      GGA ATT GAA GAT TAC ATC AAT GAA TTC AGC ACG AAA AAG TGC TCC
       G   I   E   D   Y   I   N   E   F   S   T   K   K   C   S 1580             1590             1600             1610             1620
       |                |                |                |                |
CCC TGC CAA AAC GGA GGC ACT GCA CTT CTG ATG GAT GGC CAG TGT
 P   C   Q   N   G   G   T   A   L   L   M   D   G   Q   C 1630             1640             1650             1660
                |                |                |                |
      TTG TGT ACC TGC CCG TTT ATG TTC GAG GGG ATT GCC TGT GAA ATC
       L   C   T   C   P   F   M   F   E   G   I   A   C   E   I 1670             1680             1690             1700             1710
       |                |                |                |                |
TCC AAA CGA AAA CTG GCT TAA GGA TTG CCA GCC CCC ACC CCC ACC
 S   K   R   K   L   A   -   G   L   P   A   P   T   P   T 1720             1730             1740             1750
                |                |                |                |
      CCC CAA AAT GCA ACT GTT GAG TTC CCT GAG CTC AAA TGG AAG AAA
       P   Q   N   A   T   V   E   F   P   E   L   K   W   K   K 1760             1770             1780             1790             1800
       |                |                |                |                |
AAC AAC ACC AGG ACC TTC CAA TGT AAG ATC CTG CCC TGC CTG GAG
 N   N   T   R   T   F   Q   C   K   I   L   P   C   L   E 1810             1820             1830             1840
                |                |                |                |
      ATA GTC CTT GCT GGC ACA TGA AAA GCA ACA TGT TTC ATG AAA ACC
       I   V   L   A   G   T   -   K   A   T   C   F   M   K   T 1850             1860             1870             1880             1890
       |                |                |                |                |
CTA CCA ACC TCT GAA GCC TCG CTC TCT CTC TGG TCT GCA ATG CCT
 L   P   T   S   E   A   S   L   S   L   W   S   A   M   P 1900             1910             1920             1930
                |                |                |                |
      GTT TTT CCC CAT AAA CCC CTG TAA TGT TTC CAT TTT TAT GTA ATG
       V   F   P   H   K   P   L   -   C   F   H   F   Y   L   M 1940             1950             1960             1970             1980
       |                |                |                |                |
AAG AGA CAG CCA TGA GCT GTG CCA GAA GTG TTT TCT CCC ACA GCC
 K   R   Q   P   -   A   V   P   E   V   F   S   P   T   A 1990             2000             2010             2020
                |                |                |                |
      AAT GCC AGC CTC TTG CTA ATA AAA GAA AAT AAA ATT CAA AAA AAA
       N   A   S   L   L   L   I   K   E   N   K   I   Q   K   K

2030
       |
AAA AAA AAA
 K   K   K
```

I claim:

1. A composition comprising molecules specifically modulating binding of CD59 to C9 selected from the group of molecules consisting of peptides of between 26 and 30 amino acids which bind to CD59 and molecules binding to C9 amino acid residues 359 to 384 (amino acid residues 381–406 of SEQ. ID NO. 5).

2. The composition of claim 1 comprising molecules selected from the group of molecules consisting of peptides of between 26 and 30 amino acids comprising hu C9 amino acid residues 359 to 384 (amino acid residues 381–406 of SEQ. ID NO. 5), anti-idiotypic antibodies immunoreactive with C9 amino acid residues 359 to 384 (amino acid residues 381–406 of SEQ. ID NO. 5), and covalently cyclized peptides comprising hu C9 amino acid residues 359 to 384 (amino acid residues 381–406 of SEQ. ID NO. 5).

3. The composition of claim 2 wherein the molecules are a peptide including amino acid residues 359 to 384 of hu C9 (amino acid residues 381–406 of SEQ. ID NO. 5).

4. The composition of claim 1 further comprising a pharmaceutically acceptable carrier for administration to patients in need thereof.

* * * * *